US009809838B2

(12) United States Patent
Walt et al.

(10) Patent No.: US 9,809,838 B2
(45) Date of Patent: Nov. 7, 2017

(54) METHODS FOR DETERMINING THE CONCENTRATION OF AN ANALYTE IN SOLUTION

(71) Applicant: Trustees of Tufts College, Medford, MA (US)

(72) Inventors: David R. Walt, Boston, MA (US); David M. Rissin, Somerville, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 15/290,939

(22) Filed: Oct. 11, 2016

(65) Prior Publication Data

US 2017/0159104 A1 Jun. 8, 2017

Related U.S. Application Data

(63) Continuation of application No. 12/675,686, filed as application No. PCT/US2007/019184 on Aug. 30, 2007, now abandoned.

(51) Int. Cl.
*C12Q 1/00* (2006.01)
*C12Q 1/40* (2006.01)
*G01N 33/68* (2006.01)

(52) U.S. Cl.
CPC .......... *C12Q 1/40* (2013.01); *G01N 33/6854* (2013.01); *G01N 2333/522* (2013.01); *G01N 2333/938* (2013.01)

(58) Field of Classification Search
None
See application file for complete search history.

(56) References Cited

U.S. PATENT DOCUMENTS

| | | |
|---|---|---|
| 3,712,986 A | 1/1973 | Collings |
| 4,200,110 A | 4/1980 | Peterson et al. |
| 4,232,119 A | 11/1980 | Carlsson et al. |
| 4,631,211 A | 12/1986 | Houghten |
| 4,780,421 A | 10/1988 | Kameda et al. |
| 4,883,642 A | 11/1989 | Bisconte |
| 4,907,037 A | 3/1990 | Boisde et al. |
| 4,924,870 A | 5/1990 | Wlodarczyk et al. |
| 4,962,037 A | 10/1990 | Jett et al. |
| 5,026,159 A | 6/1991 | Allen et al. |
| 5,028,535 A | 7/1991 | Buechler et al. |
| 5,089,391 A | 2/1992 | Buechler et al. |
| 5,091,300 A | 2/1992 | Hurni et al. |
| 5,108,961 A | 4/1992 | Zhong et al. |
| 5,152,816 A | 10/1992 | Berkey |
| 5,190,857 A | 3/1993 | Allen et al. |
| 5,196,306 A | 3/1993 | Bobrow et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,298,741 A | 3/1994 | Walt et al. |
| 5,315,375 A | 5/1994 | Allen |
| 5,320,814 A | 6/1994 | Walt et al. |
| 5,329,461 A | 7/1994 | Allen et al. |
| 5,374,395 A | 12/1994 | Robinson et al. |
| 5,405,783 A | 4/1995 | Pirrung et al. |
| 5,445,934 A | 8/1995 | Fodor et al. |
| 5,468,846 A | 11/1995 | Ichikawa et al. |
| 5,488,567 A | 1/1996 | Allen et al. |
| 5,512,490 A | 4/1996 | Walt et al. |
| 5,532,138 A | 7/1996 | Singh et al. |
| 5,532,379 A | 7/1996 | Fujimoto |
| 5,545,531 A | 8/1996 | Rava et al. |
| 5,583,001 A | 12/1996 | Bobrow et al. |
| 5,620,850 A | 4/1997 | Bamdad et al. |
| 5,633,972 A | 5/1997 | Walt et al. |
| 5,690,894 A | 11/1997 | Pinkel et al. |
| 5,700,637 A | 12/1997 | Southern |
| 5,731,158 A | 3/1998 | Bobrow et al. |
| 5,770,455 A | 6/1998 | Cargill et al. |
| 5,807,522 A | 9/1998 | Brown et al. |
| 5,814,524 A | 9/1998 | Walt et al. |
| 5,885,529 A | 3/1999 | Babson et al. |
| 5,900,481 A | 5/1999 | Lough et al. |
| 5,981,180 A | 11/1999 | Chandler et al. |
| 6,001,564 A | 12/1999 | Bergeron et al. |
| 6,007,690 A | 12/1999 | Nelson et al. |
| 6,013,445 A | 1/2000 | Albrecht et al. |
| 6,023,540 A | 2/2000 | Walt et al. |
| 6,133,436 A | 10/2000 | Koster et al. |
| 6,143,496 A | 11/2000 | Brown et al. |

(Continued)

FOREIGN PATENT DOCUMENTS

| | | |
|---|---|---|
| AU | 199956253 B2 | 3/2000 |
| CN | 1635146 A | 7/2005 |

(Continued)

OTHER PUBLICATIONS

Rissin et al (2006 JACS 128:6286-7).*
Office Communication for EP Application No. 07837608.4 filed Aug. 30, 2007, published as EP 2201374 dated Jun. 30, 2010, which Office Communication is dated May 6, 2010, and claims as pending for EP Application No. 07837608.4 dated May 6, 2010.
Response to Office Communication for EP Application No. 07837608.4 filed Aug. 30, 2007, published as EP 2201374 dated Jun. 30, 2010, which Response is dated Jun. 15, 2010, and claims as pending for EP Application No. 07837608.4 dated Jun. 15, 2010.
Office Communication for EP Application No. 07837608.4 filed Aug. 30, 2007, published as EP 2201374 dated Jun. 30, 2010, which Office Communication is dated Dec. 1, 2010, and claims as pending for EP Application No. 07837608.4 dated Dec. 1, 2010.

(Continued)

*Primary Examiner* — Christopher M Gross
(74) *Attorney, Agent, or Firm* — Wolf, Greenfield & Sacks, P.C.

(57) ABSTRACT

Disclosed is a method for measuring the concentration of an analyte or analytes in a solution. Although the methods can be conducted using a number of different assay formats, in one embodiment, the assays are conducted in reaction vessels defined, at least in part, by the distal ends of fiber optic strands.

10 Claims, 11 Drawing Sheets

(56) References Cited

U.S. PATENT DOCUMENTS

| | | |
|---|---|---|
| 6,156,270 A | 12/2000 | Buechler |
| 6,174,695 B1 | 1/2001 | Hammock et al. |
| 6,210,910 B1 | 4/2001 | Walt et al. |
| 6,266,459 B1 | 7/2001 | Walt et al. |
| 6,285,807 B1 | 9/2001 | Walt et al. |
| 6,327,410 B1 | 12/2001 | Walt et al. |
| 6,329,139 B1 | 12/2001 | Nova et al. |
| 6,368,874 B1 | 4/2002 | Gallop et al. |
| 6,377,721 B1 | 4/2002 | Walt et al. |
| 6,388,746 B1 | 5/2002 | Eriksson et al. |
| 6,396,995 B1 | 5/2002 | Stuelpnagel et al. |
| 6,406,845 B1 | 6/2002 | Walt et al. |
| 6,432,630 B1 | 8/2002 | Blankenstein |
| 6,482,593 B2 | 11/2002 | Walt et al. |
| 6,582,908 B2 | 6/2003 | Fodor et al. |
| 6,602,702 B1 | 8/2003 | McDevitt et al. |
| 6,620,584 B1 | 9/2003 | Chee et al. |
| 6,635,452 B1 | 10/2003 | Monforte et al. |
| 6,667,159 B1 | 12/2003 | Walt et al. |
| 6,713,309 B1 | 3/2004 | Anderson et al. |
| 6,714,303 B2 | 3/2004 | Ivarsson |
| 6,821,449 B2 | 11/2004 | Caplen et al. |
| 6,838,051 B2 | 1/2005 | Marquiss et al. |
| 6,858,394 B1 | 2/2005 | Chee et al. |
| 6,859,570 B2 | 2/2005 | Walt et al. |
| 6,878,345 B1 | 4/2005 | Astle |
| 6,929,924 B2 | 8/2005 | Bouanani et al. |
| 6,942,968 B1 | 9/2005 | Dickinson et al. |
| 6,943,034 B1 | 9/2005 | Winkler et al. |
| 6,991,939 B2 | 1/2006 | Walt et al. |
| 6,999,657 B2 | 2/2006 | Walt |
| 7,056,746 B2 | 6/2006 | Seul et al. |
| 7,060,431 B2 | 6/2006 | Chee et al. |
| 7,115,884 B1 | 10/2006 | Walt et al. |
| 7,211,390 B2 | 5/2007 | Rothberg et al. |
| 7,244,559 B2 | 7/2007 | Rothberg et al. |
| 7,250,267 B2 | 7/2007 | Walt et al. |
| 7,264,929 B2 | 9/2007 | Rothberg et al. |
| 7,348,181 B2 | 3/2008 | Walt et al. |
| 7,480,433 B2 | 1/2009 | Walt et al. |
| 7,572,581 B2 | 8/2009 | Gelfand et al. |
| 7,651,841 B2 | 1/2010 | Song et al. |
| 7,759,062 B2 | 7/2010 | Allawi et al. |
| 7,776,553 B2 | 8/2010 | Love et al. |
| 7,838,250 B1 | 11/2010 | Goix et al. |
| 8,222,047 B2 | 7/2012 | Duffy et al. |
| 8,236,574 B2 | 8/2012 | Duffy et al. |
| 8,415,171 B2 | 4/2013 | Rissin et al. |
| 8,460,878 B2 | 6/2013 | Walt et al. |
| 8,460,879 B2 | 6/2013 | Walt et al. |
| 8,492,098 B2 | 7/2013 | Walt et al. |
| 8,846,415 B2 | 9/2014 | Duffy et al. |
| 9,110,025 B2 | 8/2015 | Rissin et al. |
| 9,310,360 B2 | 4/2016 | Duffy et al. |
| 9,395,359 B2 | 7/2016 | Walt et al. |
| 9,482,662 B2 | 11/2016 | Duffy et al. |
| 9,551,663 B2 | 1/2017 | Rissin et al. |
| 2002/0009391 A1 | 1/2002 | Marquiss et al. |
| 2002/0090650 A1 | 7/2002 | Empedocles et al. |
| 2002/0122612 A1 | 9/2002 | Walt et al. |
| 2003/0027126 A1 | 2/2003 | Walt et al. |
| 2003/0091475 A1 | 5/2003 | Yu et al. |
| 2003/0104361 A1 | 6/2003 | Weininger et al. |
| 2003/0143580 A1 | 7/2003 | Straus |
| 2003/0198573 A1 | 10/2003 | Forood et al. |
| 2004/0038426 A1 | 2/2004 | Manalis |
| 2004/0043502 A1 | 3/2004 | Song et al. |
| 2004/0053322 A1 | 3/2004 | McDevitt et al. |
| 2004/0071599 A1 | 4/2004 | Rusch et al. |
| 2004/0072278 A1 | 4/2004 | Chou et al. |
| 2004/0086426 A1 | 5/2004 | Vann et al. |
| 2004/0101918 A1 | 5/2004 | Cauci |
| 2004/0142386 A1 | 7/2004 | Rigler et al. |
| 2004/0248325 A1 | 12/2004 | Bukusoglu |
| 2004/0253624 A1 | 12/2004 | Smith et al. |
| 2004/0259237 A1 | 12/2004 | Kellogg et al. |
| 2005/0112634 A1 | 5/2005 | Woudenberg et al. |
| 2005/0112655 A1 | 5/2005 | Banerjee et al. |
| 2005/0129581 A1 | 6/2005 | McBride et al. |
| 2005/0130173 A1 | 6/2005 | Leamon et al. |
| 2005/0130188 A1 | 6/2005 | Walt et al. |
| 2005/0131650 A1 | 6/2005 | Andersson et al. |
| 2005/0164289 A1 | 7/2005 | Quate et al. |
| 2005/0221281 A1 | 10/2005 | Ho |
| 2005/0226780 A1 | 10/2005 | Sandell et al. |
| 2005/0244308 A1 | 11/2005 | Tanaami et al. |
| 2005/0266433 A1 | 12/2005 | Kapur et al. |
| 2006/0006067 A1 | 1/2006 | Unger |
| 2006/0013543 A1 | 1/2006 | Walt et al. |
| 2006/0040297 A1 | 2/2006 | Leamon et al. |
| 2006/0068409 A1 | 3/2006 | Phan et al. |
| 2006/0078998 A1 | 4/2006 | Puskas et al. |
| 2006/0084183 A1 | 4/2006 | Henriksen |
| 2006/0139635 A1 | 6/2006 | Kersey et al. |
| 2007/0040095 A1 | 2/2007 | Walt et al. |
| 2007/0059754 A1 | 3/2007 | Kordunsky et al. |
| 2007/0074972 A1 | 4/2007 | Nassef et al. |
| 2007/0116607 A1 | 5/2007 | Wang et al. |
| 2007/0259381 A1 | 11/2007 | Rissin et al. |
| 2007/0259385 A1 | 11/2007 | Rissin et al. |
| 2007/0259448 A1 | 11/2007 | Rissin et al. |
| 2008/0032324 A1 | 2/2008 | Walt et al. |
| 2008/0064113 A1 | 3/2008 | Goix et al. |
| 2008/0269069 A1 | 10/2008 | Bacher et al. |
| 2009/0036324 A1 | 2/2009 | Fan et al. |
| 2009/0087860 A1 | 4/2009 | Todd et al. |
| 2009/0142755 A1 | 6/2009 | Albitar |
| 2009/0149341 A1 | 6/2009 | Walt et al. |
| 2009/0156425 A1 | 6/2009 | Walt et al. |
| 2009/0170728 A1 | 7/2009 | Walt et al. |
| 2009/0239308 A1 | 9/2009 | Dube et al. |
| 2009/0254180 A1 | 10/2009 | Pazanowski et al. |
| 2009/0289834 A1 | 11/2009 | Devensky |
| 2009/0307772 A1 | 12/2009 | Markham et al. |
| 2010/0075355 A1 | 3/2010 | Duffy et al. |
| 2010/0075407 A1 | 3/2010 | Duffy et al. |
| 2010/0075439 A1 | 3/2010 | Duffy et al. |
| 2010/0075862 A1 | 3/2010 | Duffy et al. |
| 2010/0140289 A1 | 6/2010 | Knobel et al. |
| 2010/0189338 A1 | 7/2010 | Lin et al. |
| 2010/0192573 A1 | 8/2010 | Hamilton et al. |
| 2010/0204335 A1 | 8/2010 | Beddingfield et al. |
| 2010/0225913 A1 | 9/2010 | Trainer |
| 2010/0227379 A1 | 9/2010 | Wo et al. |
| 2010/0329929 A1 | 12/2010 | Goix et al. |
| 2011/0037463 A1 | 2/2011 | Bertacco et al. |
| 2011/0183330 A1 | 7/2011 | Lo et al. |
| 2011/0195852 A1 | 8/2011 | Walt et al. |
| 2011/0212462 A1 | 9/2011 | Duffy et al. |
| 2011/0212537 A1 | 9/2011 | Rissin et al. |
| 2011/0212848 A1 | 9/2011 | Duffy et al. |
| 2011/0245097 A1 | 10/2011 | Rissin et al. |
| 2012/0183967 A1 | 7/2012 | Dressman et al. |
| 2012/0196774 A1 | 8/2012 | Fournier et al. |
| 2012/0214160 A1 | 8/2012 | Deng et al. |
| 2012/0277114 A1 | 11/2012 | Duffy et al. |
| 2012/0289428 A1 | 11/2012 | Duffy et al. |
| 2013/0165342 A1 | 6/2013 | Rissin et al. |
| 2013/0345078 A1 | 12/2013 | Walt et al. |
| 2014/0094386 A1 | 4/2014 | Wilson et al. |
| 2014/0227720 A1 | 8/2014 | Wilson et al. |
| 2014/0302532 A1 | 10/2014 | Wilson et al. |
| 2015/0233905 A1 | 8/2015 | Walt et al. |
| 2015/0353997 A1 | 12/2015 | Duffy et al. |
| 2015/0355182 A1 | 12/2015 | Rissin et al. |
| 2016/0123969 A1 | 5/2016 | Rissin et al. |
| 2016/0258959 A1 | 9/2016 | Wilson et al. |
| 2017/0038390 A1 | 2/2017 | Walt et al. |

FOREIGN PATENT DOCUMENTS

| | | |
|---|---|---|
| CN | 1950520 A | 4/2007 |
| CN | 101351564 A | 1/2009 |
| CN | 101529227 A | 9/2009 |

(56) References Cited

FOREIGN PATENT DOCUMENTS

| | | |
|---|---|---|
| CN | 101541974 A | 9/2009 |
| DE | 19540098 A1 | 4/1997 |
| EP | 0 805 215 A2 | 11/1997 |
| EP | 1 180 679 A1 | 2/2002 |
| EP | 1 259 810 B1 | 11/2006 |
| EP | 1 721 657 A1 | 11/2006 |
| EP | 2 267 451 A2 | 12/2010 |
| EP | 2 201 374 B1 | 10/2015 |
| JP | 2001/269196 A | 10/2001 |
| JP | 2002-506200 A | 2/2002 |
| JP | 2002-525587 A | 8/2002 |
| JP | 2002-526743 A | 8/2002 |
| JP | 2004-354164 A | 12/2004 |
| JP | 2005-518553 A | 6/2005 |
| JP | 2006-511792 A | 4/2006 |
| WO | WO 88/05533 A1 | 7/1988 |
| WO | WO 93/06121 A1 | 4/1993 |
| WO | WO 93/24517 A2 | 12/1993 |
| WO | WO 95/25116 A1 | 9/1995 |
| WO | WO 95/32425 A1 | 11/1995 |
| WO | WO 95/35506 A2 | 12/1995 |
| WO | WO 97/27326 A1 | 7/1997 |
| WO | WO 98/50782 A2 | 11/1998 |
| WO | WO 99/45357 A2 | 9/1999 |
| WO | WO 99/58948 A2 | 11/1999 |
| WO | WO 00/04372 A1 | 1/2000 |
| WO | WO 00/47996 A2 | 8/2000 |
| WO | WO 01/57520 A2 | 8/2001 |
| WO | WO 03/054142 A2 | 7/2003 |
| WO | WO 03/073817 A1 | 9/2003 |
| WO | WO 2004/065000 A1 | 8/2004 |
| WO | WO 2004/083443 A1 | 9/2004 |
| WO | WO 2005/019419 A2 | 3/2005 |
| WO | WO 2005/023414 A1 | 3/2005 |
| WO | WO 2005/033283 A2 | 4/2005 |
| WO | WO 2005/054431 A2 | 6/2005 |
| WO | WO 2006/007726 A1 | 1/2006 |
| WO | WO 2006/055739 A2 | 5/2006 |
| WO | WO 2006/078289 A2 | 7/2006 |
| WO | WO 2006/102297 A1 | 9/2006 |
| WO | WO 2006/108180 A2 | 10/2006 |
| WO | WO 2007/044091 A2 | 4/2007 |
| WO | WO 2007/044974 A2 | 4/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/084192 A2 | 7/2007 |
| WO | WO 2007/098148 A2 | 8/2007 |
| WO | WO 2007/114947 A2 | 10/2007 |
| WO | WO 2008/048371 A2 | 4/2008 |
| WO | WO 2009/029073 A1 | 3/2009 |
| WO | WO 2010/039180 A2 | 4/2010 |
| WO | WO 2011/109364 A2 | 9/2011 |
| WO | WO 2011/109372 A1 | 9/2011 |

OTHER PUBLICATIONS

Response to Office Communication for EP Application No. 07837608.4 filed Aug. 30, 2007, published as EP 2201374 dated Jun. 30, 2010, which Response is dated Jun. 9, 2011, and claims as pending for EP Application No. 07837608.4 dated Jun. 9, 2011.
Office Communication for EP Application No. 07837608.4 filed Aug. 30, 2007, published as EP 2201374 dated Jun. 30, 2010, which Office Communication is dated Dec. 12, 2011, and claims as pending for EP Application No. 07837608.4 dated Dec. 12, 2011.
Response to Office Communication for EP Application No. 07837608.4 filed Aug. 30, 2007, published as EP 2201374 dated Jun. 30, 2010, which Response is dated Jun. 21, 2012, and claims as pending for EP Application No. 07837608.4 dated Jun. 21, 2012.
Office Communication for EP Application No. 07837608.4, filed Aug. 30, 2007, published as EP 2201374, which Office Communication is dated Sep. 6, 2012, and claims as pending for EP Application No. 07837608.4 dated Sep. 6, 2012.
Response to Office Communication for EP Application No. 07837608.4 filed Aug. 30, 2007, published as EP 2201374 dated Jun. 30, 2010, which Response is dated May 14, 2013, and claims as pending for EP Application No. 07837608.4 dated May 14, 2013.
Office Communication for EP Application No. 07837608.4, filed Aug. 30, 2007, which Office Communication is dated Jan. 16, 2014, and claims as pending for EP Application No. 07837608.4 dated May 14, 2013.
Response to Office Communication for EP Application No. 07837608.4 filed Aug. 30, 2007, published as EP 2201374 dated Jun. 30, 2010, which Response is dated Jul. 28, 2014, and claims as pending for EP Application No. 07837608.4 dated Jul. 28, 2014.
Office Communication for EP Application No. 07837608.4, filed Aug. 30, 2007, which Office Communication is dated Sep. 16, 2014, and claims as pending for EP Application No. 07837608.4 dated Jul. 28, 2014.
Response to Office Communication for EP Application No. 07837608.4 filed Aug. 30, 2007, published as EP 2201374 dated Jun. 30, 2010, which Response is dated Jan. 21, 2015, and amended description for EP Application No. 07837608.4.
Intention to Grant for EP Application No. 07837608.4, filed Aug. 30, 2007, which Intention to Grant is dated Apr. 24, 2015, and claims as allowed for EP Application No. 07837608.4.
International Search Report and Written Opinion for International Application No. PCT/US2007/019184, dated Jun. 19, 2008.
International Preliminary Report on Patentability, Chapter 1, for International Application No. PCT/US2007/019184, dated Mar. 11, 2010.
Blicharz et al., Fiber-optic microsphere-based antibody array for the analysis of inflammatory cytokines in saliva. Anal. Chem. 2009;81(6):2106-14.
Prabhakar et al., Simultaneous quantification of proinflammatory cytokines in human plasma using the LabMAP assay. J Immunol Methods. Feb. 1, 2002;260(1-2):207-18.
Rissin et al., Digital concentration readout of single enzyme molecules using femtoliter arrays and Poisson statistics. Nano Lett. Mar. 2006; 6(3):520-3.
Rissin et al., Digital readout of target binding with attomole detection limits via enzyme amplification in femtoliter arrays. J Am Chem Soc. May 17, 2006; 128(19):6286-7.
Communication pursuant to Article 94(3) EPC for EP Application No. 07837608.4-1402, filed Aug. 30, 2007, which Office Communication is dated Jan. 16, 2014, and claims as pending for EP Application No. 07837608.4-1402 dated May 14, 2013.
Communication pursuant to Article 94(3) EPC for EP Application No. 07837608.4-1402, filed Aug. 30, 2007, which Office Communication is dated Sep. 16, 2014, and claims as pending for EP Application No. 07837608.4-1402 dated Jul. 28, 2014.
Communication under Rule 71(3) EPC for EP Application No. 07837608.4-1402, filed Aug. 30, 2007, which Office Communication is dated Apr. 24, 2015, and claims as allowed for EP Application No. 07837608.4-1402.
Office Communication for CA Application No. 2,734,029, filed Aug. 7, 2007, which Office Communication is dated Oct. 1, 2013, and claims as pending for Canadian Application No. 2,734,029.
Office Communication for CA Application No. 2,734,029, filed Aug. 7, 2007, which Office Communication is dated Aug. 5, 2014, and claims as pending for Canadian Application No. 2,734,029 dated Apr. 1, 2014.
Notice of Allowance for CA Application No. 2,734,029, filed Aug. 30, 2007, which Notice of Allowance is dated Jul. 16, 2015, and claims as granted for CA Application No. 2,734,029.
Translation of Office Communication for Japanese Application No. 2010-522877 filed Aug. 30, 2007, which Office Communication is dated Jan. 17, 2012, and translation of claims as pending for Japanese Application No. 2010-522877 dated Jan. 17, 2012.
Decision to Grant for Japanese Application No. 2010-522877 filed Aug. 30, 2007, which Decision to Grant is dated Feb. 18, 2014, and translation of claims as pending for Japanese Application No. 2010-522877 dated Jun. 5, 2013.
Office Communication for U.S. Appl. No. 12/675,686, filed Apr. 4, 2011, which Office Communication is dated Nov. 30, 2015, and claims as pending for U.S. Appl. No. 12/675,686 dated Sep. 3, 2015.

(56) References Cited

OTHER PUBLICATIONS

Office Communication for U.S. Appl. No. 12/675,686, filed Apr. 4, 2011, which Office Communication is dated Jul. 8, 2016, and claims as pending for U.S. Appl. No. 12/675,686 dated Sep. 3, 2015.
Notice of Allowance for CA Application No. 2,643,993, filed Feb. 20, 2007, which Notice of Allowance is dated Apr. 20, 2015, and claims as allowed for CA Application No. 2,643,993.
Office Communication for EP Application No. 07751131.9 filed Feb. 20, 2007, published as EP 1996717 dated Dec. 3, 2008, which Office Communication is dated Oct. 30, 2008, and claims as pending for EP Application No. 07837608.4 dated Oct. 30, 2008.
Response to Office Communication for EP Application No. 07751131.9 filed Feb. 20, 2007, published as EP 1996717 dated Dec. 3, 2008, which Response is dated Dec. 9, 2008, and claims as pending for EP Application No. 07751131.9 dated Dec. 9, 2008.
European Search Report for European Application No. 07751131.9, dated Sep. 8, 2009.
Office Communication for EP Application No. 07751131.9 filed Feb. 20, 2007, published as EP 1996717 dated Dec. 3, 2008, which Office Communication is dated Sep. 8, 2009, and claims as pending for EP Application No. 07837608.4 dated Sep. 8, 2009.
Response to Office Communication for EP Application No. 07751131.9 filed Feb. 20, 2007, published as EP 1996717 dated Dec. 3, 2008, which Response is dated Dec. 10, 2009, and claims as pending for EP Application No. 07751131.9 dated Dec. 10, 2009.
Office Communication for EP Application No. 07751131.9 filed Feb. 20, 2007, published as EP 1996717 dated Dec. 3, 2008, which Office Communication is dated Jul. 20, 2010, and claims as pending for EP Application No. 07837608.4 dated Jul. 20, 2010.
Response to Office Communication for EP Application No. 07751131.9 filed Feb. 20, 2007, published as EP 1996717 dated Dec. 3, 2008, which Response is dated Jan. 19, 2011, and claims as pending for EP Application No. 07751131.9 dated Jan. 19, 2011.
Office Communication for EP Application No. 07751131.9 filed Feb. 20, 2007, published as Ep 1996717 on Dec. 3, 2008, which Office Communication is dated Nov. 30, 2011, and claims as pending for Ep Application No. 07837608.4 as of Nov. 30, 2011 (T0605.70005EP00).
Office Communication for EP Application No. 07751131.9, filed Feb. 20, 2007, which Office Communication is dated Mar. 28, 2013, and claims as allowed for European Application No. 07751131.9 dated Mar. 28, 2013.
Office Communication for EP Application No. 07751131.9, filed Feb. 20, 2007, which Office Communication is dated Apr. 5, 2013, and claims as allowed for European Application No. 07751131.9 dated Apr. 5, 2013.
Intention to Grant for EP Application No. 07751131.9, filed Feb. 20, 2007, which Intention to Grant is dated May 27, 2014, and claims as allowed for European Application No. 07751131.9 dated Aug. 2, 2013.
Extended European Search Report for EP Application No. 12177276.8 dated Nov. 26, 2012.
Office Communication for EP Application No. 12177276.8, filed Feb. 20, 2007, which Office Communication is dated Apr. 28, 2014, and claims as allowed for European Application No. 12177276.8 dated Jun. 26, 2013.
Office Communication for EP Application No. 12177276.8, filed Feb. 20, 2007, which Office Communication is dated Dec. 23, 2014, and claims as pending for EP Application No. 12177276.8 dated Sep. 8, 2014.
Intention to Grant for EP Application No. 12177276.8, filed Feb. 20, 2007, which Intention to Grant is dated Jan. 29, 2016, and claims as granted for EP Application No. 12177276.8.
Intention to Grant for EP Application No. 12177276.8 filed Feb. 20, 2007, which Intention to Grant is dated May 18, 2016, and claims as granted for EP Application No. 12177276.8.
Office Communication for JP Application No. 2011-034007, filed Feb. 20, 2007, which Office Communication is dated Feb. 19, 2013, and claims as pending for Japanese Application No. 2011-034007 dated Feb. 19, 2013.
Decision to Grant for JP Application No. 2011-034007, filed Feb. 20, 2007, which Decision to Grant is dated Oct. 8, 2013, and claims as allowed for JP Application No. 2011-034007.
Office Communication for U.S. Appl. No. 11/707,385, filed Feb. 16, 2007, published as US 2007-0259448 dated Nov. 8, 2007, which Office Communication is dated Mar. 16, 2009, and claims as pending for U.S. Appl. No. 11/707,385 dated Mar. 16, 2009.
Office Communication for U.S. Appl. No. 11/707,385, filed Feb. 16, 2007, published as US 2007-0259448 dated Nov. 8, 2007, which Office Communication is dated Jan. 26, 2010, and claims as pending for U.S. Appl. No. 11/707,385 dated Jan. 26, 2010.
Office Communication for U.S. Appl. No. 11/707,385, filed Feb. 16, 2007, published as US 2007-0259448, which Office Communication is dated Sep. 27, 2012, and claims as pending for U.S. Appl. 11/707,385 dated Sep. 27, 2012.
Notice of Allowance for U.S. Appl. No. 11/707,385, filed Feb. 16, 2007, published as US-2007-0259448, which Notice of Allowance is dated Feb. 25, 2013, and claims as allowed for U.S. Appl. No. 11/707,385 dated Feb. 25, 2013.
Office Communication for U.S. Appl. No. 11/707,383, filed Feb. 16, 2007, published as US 2007-0259385 dated Nov. 8, 2007, which Office Communication is dated Mar. 16, 2009, and claims as pending for U.S. Appl. No. 11/707,383 dated Mar. 16, 2009.
Office Communication for U.S. Appl. No. 11/707,383, filed Feb. 16, 2007, published as US 2007-0259385 dated Nov. 8, 2007, which Office Communication is dated Nov. 27, 2009, and claims as pending for U.S. Appl. No. 11/707,383 dated Nov. 27, 2009.
Office Communication for U.S. Appl. No. 11/707,383, filed Feb. 16, 2007, published as 2007-0259385, which Office Communication is dated Sep. 27, 2012, and claims as pending for U.S. Appl. No. 11/707,383 dated Sep. 27, 2012.
Notice of Allowance for U.S. Appl. No. 11/707,383, filed Feb. 16, 2007, published as US 2007-0259385, which Notice of Allowance is dated Feb. 8, 2013, and claims as allowed for U.S. Appl. No. 11/707,383 dated Feb. 8, 2013.
Office Communication for U.S. Appl. No. 11/707,384, filed Feb. 16, 2007, published as US 2007-0259381 dated Nov. 8, 2007, which Office Communication is dated Mar. 16, 2009, and claims as pending for U.S. Appl. No. 11/707,384 dated Mar. 16, 2009.
Office Communication for U.S. Appl. No. 11/707,384, filed Feb. 16, 2007, published as US 2007-0259381 dated Nov. 8, 2007, which Office Communication is dated Dec. 2, 2009, and claims as pending for U.S. Appl. No. 11/707,384 dated Dec. 2, 2009.
Office Communication for U.S. Appl. No. 14/638,245, filed Mar. 4, 2015, which Office Communication is dated Aug. 20, 2015, and claims as filed for U.S. Appl. No. 14/638,245.
Notice of Allowance for U.S. Appl. No. 14/638,245, filed Mar. 4, 2015, which Notice of Allowance is dated Mar. 17, 2016, and claims as allowed for U.S. Appl. No. 14/638,245.
International Search Report and Written Opinion for International Application No. PCT/US2007/004349, dated Aug. 21, 2008.
International Preliminary Report on Patentability, Chapter 1, for International Application No. PCT/US2007/004349 dated Sep. 25, 2008.
International Preliminary Report on Patentability, Chapter 2, for International Application No. PCT/US2007/004349 dated Mar. 23, 2009.
Office Communication for U.S. Appl. No. 12/236,484, filed Sep. 23, 2008, published as US 2010-0075862 dated Mar. 25, 2010, which Office Communication is dated Sep. 9, 2010, and claims as pending for U.S. Appl. No. 12/236,484 dated Sep. 9, 2010.
Office Communication for U.S. Appl. No. 12/236,484, filed Sep. 23, 2008, published as US 2010-0075862 dated Mar. 25, 2010, which Office Communication is dated Apr. 13, 2011, and claims as pending for U.S. Appl. No. 12/236,484 dated Apr. 13, 2011.
International Search Report and Written Opinion for International Application No. PCT/US2009/005250, dated Mar. 22, 2010.
Office Communication for U.S. Appl. No. 12/236,486, filed Sep. 23, 2008, published as US 2010-0075407 dated Mar. 25, 2010, which Office Communication is dated Nov. 23, 2011, and claims as pending for U.S. Appl. No. 12/236,486 dated Nov. 23, 2008.
International Search Report and Written Opinion for International Application No. PCT/US2009/005248, dated Mar. 1, 2010.

(56) References Cited

OTHER PUBLICATIONS

Office Communication for U.S. Appl. No. 12/236,488, filed Sep. 23, 2008, published as US 2010-0075439 dated Mar. 25, 2010, which Office Communication is dated Aug. 2, 2010, and claims as pending for U.S. Appl. No. 12/236,488 dated Aug. 2, 2010.
International Search Report and Written Opinion for International Application No. PCT/US2011/026645, dated Nov. 24, 2011.
International Search Report and Written Opinion for International Application No. PCT/US2011/026657, dated May 24, 2011.
International Search Report and Written Opinion for International Application No. PCT/US2011/026665, dated Jul. 5, 2011.
[No Author Listed], bioMérieux and Quanterix Sign Strategic Partnership in Ultrasensitive and Multiplex Immunoassays. Quanterix Press Release. Nov. 15, 2012. 2 pages.
[No Author Listed], Does Brain Hypoxia Help Kick Off Alzheimer's Pathology? Alzheimer Research Forum. Dec. 16, 2011. http://www.alzforum.org/new/detailprint.asp?id=3002 [last accessed Jan. 30, 2012]. 4 pages.
[No Author Listed], Novel test following prostate surgery could detect cancer recurrence earlier. AACR Press Release. Sep. 29, 2010. Last accessed at http://www.aacr.org/home/public--media/aacr-press-releases.aspx?d=2072 on Jan. 31, 2012. 2 pages.
[No Author Listed], Pittcon Announces 2010 Technical Program: Webcast of Selected Symposia. Press Release. Oct. 15, 2009. http://archive.constantcontact.com/fs033/1102032821298/archive/1102745632000.html [last accessed Jan. 31, 2012]. 2 pages.
[No Author Listed], Quanterix and STRATEC Announce Strategic Partnership. Quanterix Press Release. Aug. 16, 2011. 2 pages.
[No Author Listed], Quanterix Announces Commercial Availability of its Simoa Single Molecule Array Technology. Quanterix Press Release. Jul. 30, 2013. 2 pages.
[No Author Listed], Quanterix corporation awarded $185,000 grant from the National Cancer Institute. Quanterix Press Release. Sep. 30, 2008. Last accessed at http://www.quanterix.com/news/pressReleases/SBIR1Grant.html on Jan. 31, 2012. 1 page.
[No Author Listed], Quanterix corporation raises $15 million in series A financing. Quanterix Press Release. Aug. 25, 2008. Last accessed at http://www.quanterix.com/news/pressReleases/seriesAFunding.html on Jan. 31, 2012. 2 pages.
[No Author Listed], Quanterix Discovers Link Between Heart Attack-induced Hypoxia and Suspected Alzheimer's Disease Pathway. Quanterix Press Release. Apr. 12, 2011. Last accessed at http://www.quanterix.com/events-news/press-releases/item/146-quanterix-discovers-link-between-heart-attack-induced-hypoxia-and-suspected-alzheimer's-disease-pathway on Sep. 20, 2012.
[No Author Listed], Quanterix Launches Multiplexed Single Molecule Immunoassay Technology to Improve Diagnosis and Potential Treatment of Complex Diseases. Quanterix Press Release. Sep. 17, 2013. 2 pages.
[No Author Listed], Quanterix to Present Poster Session on Blood-based Brain Biomarker Measurements of Sports Related Brain Injury at Neuroscience. Quanterix Press Release. Nov. 4, 2013. 1 page.
[No Author Listed], Quanterix's Simoa technology to detect blood biomarker for concussion in hockey players. Quanterix Press Release. Mar. 14, 2014. 1 page.
[No Author Listed], Quanterix's Ultrasensitive Simoa™ Technology Forges New Ground with Direct Detection of Genomic DNA in Human Blood and River Water. Quanterix Press Release. Jan. 22, 2013. 2 pages.
[No Author Listed], Quanterix's Ultrasensitive Simoa™ Technology Demonstrates Equivalence with NAT and 3,000x Improvement in Sensitivity over Conventional Immunoassays for HIV Detection. Quanterix Press Release. Oct. 11, 2012. 1 page.
[No Author Listed], Scientific Principle of Simoa™ (Single Molecule Array) Technology. Whitepaper 1.0. Jul. 19, 2013. 2 pages.
[No Author Listed], Single molecule arrays for digital detection in complex samples. Quanterix Corporation. IQT Technology Focus Day. Mar. 25, 2010. PowerPoint presentation. 30 pages.
Adams et al., Encoded fiber-optic microsphere arrays for probing protein-carbohydrate interactions. Angewandte Chemie. 2003; 115:5475-5478.
Agrawal et al., Nanometer-scale mapping and single-molecule detection with color-coded nanoparticle probes. Proc Natl Acad Sci U S A. Mar. 4, 2008;105(9):3298-303. Epub Feb. 27, 2008.
Agrawal et al., Single-bead immunoassays using magnetic microparticles and spectral-shifting quantum dots. J Agric Food Chem. May 16, 2007; 55(10):3778-82. Epub Apr. 25, 2007.
Ahn et al., Detection of *Salmonella* spp. Using microsphere-based, fiber-optic DNA microarrays. Anal Chem. Aug. 1, 2005; 77(15):5041-7.
Ahn et al., Fiber-optic microarray for simultaneous detection of multiple harmful algal bloom species. Appl Environ Microbiol. Sep. 2006; 72(9):5742-9.
Albert et al., Automatic decoding of sensor types within randomly ordered, high-density optical sensor arrays. Anal Bioanal Chem. Apr. 2002; 373(8):792-802. Epub Jul. 27, 2002.
Albert et al., Cross-reactive chemical sensor arrays. Chem Rev. Jul. 12, 2000; 100(7):2595-626.
Albert et al., Information coding in artificial olfaction multisensor arrays. Anal Chem. Aug. 15, 2003; 75(16):4161-7.
Albert et al., Optical multibead arrays for simple and complex odor discrimination. Anal Chem. Jun. 1, 2001; 73(11):2501-8.
Angenendt et al., Subnanoliter enzymatic assays on microarrays. Proteomics. Feb. 2005;5(2):420-5.
Arnaud, Observing single enzymes at work. Chemical & Engineering News. Oct. 2007; 85(44): 8.
Beer et al., On-chip, real-time, single-copy polymerase chain reaction in picoliter droplets. Anal Chem. Nov. 15, 2007;79(22):8471-5. Epub Oct. 11, 2007. Abstract only.
Bencic-Nagale et al., Extending the longevity of fluorescence-based sensor arrays using adaptive exposure. Anal Chem. Oct. 1, 2005; 77(19):6155-62.
Bhat et al., Single molecule detection in nanofluidic digital array enables accurate measurement of DNA copy number. Anal Bioanal Chem. May 2009;394(2):457-67. Epub Mar. 15, 2009.
Biran et al., Optical imaging fiber-based live bacterial cell array biosensor. Anal Biochem. Apr. 1, 2003; 315(1):106-13.
Biran et al., Optical imaging fiber-based single live cell arrays: a high-density cell assay platform. Anal Chem. Jul. 1, 2002; 74(13):3046-54.
Blake et al., Phenotypic consequences of promoter-mediated transcriptional noise. Mol Cell. Dec. 28, 2006; 24(6):853-65.
Blicharz et al., Detection of inflammatory cytokines using a fiber optic microsphere immunoassay array. *Proc. SPIE.* 2006; 6380, 638010-1-638010-6.
Blicharz et al., Use of colorimetric test strips for monitoring the effect of hemodialysis on salivary nitrite and uric acid in patients with end-stage renal disease: a proof of principle. Clin Chem. Sep. 2008; 54(9):1473-80. Epub Aug. 1, 2008.
Bourzac, Next-generation diagnostics: a startup can detect tiny traces of cancer markers in blood samples. Technol Rev. May 13, 2008. Last accessed at http://www.technologyreview.com/Biztech/20760/?a=f on Feb. 2, 2012. 2 pages.
Bowden et al., Development of a microfluidic platform with an optical imaging microarray capale of attomolar target DNA detection. Anal Chem Sep. 1, 2005; 77(17):5583-8. Epub Aug. 4, 2005.
Boyden, The chemotactic effect of mixtures of antibody and antigen on polymorphonuclear leucocytes. J Exp Med. Mar. 1, 1962;115:453-66.
Brehm-Stecher et al., Single-cell microbiology: tools, technologies, and applications. Microbiol Mol Biol Rev. Sep. 2004; 68(3):538-59.
Brogan et al., Optical fiber-based sensors: application to chemical biology. Curr Opin Chem Biol. Oct. 2005; 9(5):494-500. Epub Aug. 24, 2005.
Bronk et al., Combined imaging and chemical sensing using a single optical imaging fiber. Anal Chem. Sep. 1, 1995; 67(17):2750-7.
Bronk et al., Fabrication of patterned sensor arrays with aryl azides on a polymer-coated imaging optical fiber bundle. Anal Chem. Oct. 15, 1994; 66(20):3519-20.

(56) References Cited

OTHER PUBLICATIONS

Burton et al., A microfluidic chip-compatible bioassay based on single-molecule detection with high sensitivity and multiplexing. Lab Chip. Apr. 7, 2010; 10(7):843-51. Epub Jan. 14, 2010.

Campian, Colored and fluorescent solid supports. Innovation and Perspectives in Solid Phase Synthesis. Ed. R. Epton, Mayflower Worldwide Limited, Birmingham. Ch. 77. 1994:469-472.

Chang et al., Digital Elisa of HIV P24 capsid protein with sensitivity of nucleic acid amplification tests. 2012 AACC Meeting. Los Angeles, CA. Abstract and Poster. 2012. 2 pages.

Chang et al., Prototype digital immunoassay for troponin I with sub-femtomolar sensitivity. 2013 AACC Meeting. Houston, TX. Abstract and Poster. 2013. 2 pages.

Chang et al., Simple diffusion-constrained immunoassay for p24 protein with the sensitivity of nucleic acid amplification for detecting acute HIV infection. J Virol Methods. Mar. 2013;188(1-2):153-60. doi: 10.1016/j.jviromet.2012.08.017. Epub Oct. 2, 2012.

Chang et al., Single molecule enzyme-linked immunosorbent assays: theoretical considerations. J Immunol Methods. Apr. 30, 2012;378(1-2):102-15. doi: 10.1016/j.jim.2012.02.011. Epub Apr. 30, 2013. 28 pages.

Chen et al., Microfabricated arrays of cylindrical wells facilitate single-molecule enzymology of alpha-chymotrypsin. Biotechnol Prog. Jul.-Aug. 2009; 25(4):929-37.

Chin et al., Editor's Choice: Distinctive individualism. Science. Apr. 4, 2008;320:21.

Chon et al., Characterization of single-cell migration using a computer-aided fluorescence time-lapse videomicroscopy system. Anal Biochem. Oct. 15, 1997;252(2):246-54.

Deutsch et al., Apparatus for high-precision repetitive sequential optical measurement of living cells. Cytometry. Jul. 1, 1994; 16(3):214-26.

Dicesare et al., Individual cell migration analysis using fiber-optic bundles. Anal Bioanal Chem. May 2005; 382(1):37-43. Epub Apr. 1, 2005.

Dickinson et al., A chemical-detecting system based on a cross-reactive optical sensor array. Nature. Aug. 22, 1996; 382(6593):697-700.

Dickinson et al., Convergent, self-encoded bead sensor arrays in the design of an artificial. Anal Chem. Jun. 1, 1999; 71(11):2192-8.

Dickinson et al., Current trends in 'artificial-nose' technology. Trends Biotechnol. Jun. 1998; 16(6):250-8.

Duffy et al., Detection of prostate specific antigen (PSA) in the serum of radical prostatectomy patients at femtogram per milliliter levels using digital ELISA (AccuPSATM) based on single molecule arrays (SiMoA). AACC Meeting Poster. 2010. 1 page.

Duffy, Immunoassays with Broad Dynamic Ranges based on Combining Digital and Digitally Enhanced Analog Detecion of Enzyme Labels. Oak Ridge Conference. Presentation. Apr. 15, 2011. 16 pages.

Duffy, Single Molecule Arrays (Simoa) for Ultrasensitive Protein Detection in Companion Diagnostics. Next Generation DX Summit. Aug. 22, 2012. PowerPoint presentation. 18 slides.

Duffy, Ultra-sensitive protein detection using single molecule arrays (Simoa): the potential for detecting single molecules of botulinum toxin. The Botulinum J. 2012;2(2):164-7.

Egner et al., Tagging in combinatorial chemistry: the use of coloured and flurorescent beads. Chem Commun. 1997; 735-736.

Eid et al., Real-time DNA sequencing from single polymerase molecules. Science. Jan. 2, 2009; 323(5910):133-8. Epub Nov. 20, 2008.

Ekins et al., Single-molecule ELISA. Clin Chem. Mar. 2011;57(3):372-5. Epub Oct. 13, 2010. Papers in press. Oct. 13, 2010. pp. 1-3.

English et al., Ever-fluctuating single enzyme molecules: Michaelis-Menten equation revisited. Nat Chem Biol. Feb. 2006; 2(2):87-94. Epub Dec. 25, 2005.

Epstein et al., Combinatorial decoding: an approach for universal DNA array fabrication. J Am Chem Soc. Nov. 12, 2003; 125(45):13753-9.

Epstein et al., Fluorescence-based nucleic acid detection and microarrays. Analytica Chimica Acta. 2002; 469:3-36.

Epstein et al., High-density fiber-optic genosensor microsphere array capable of zeptomole detection limits. Anal Chem. Apr. 15, 2002; 74(8):1836-40.

Epstein et al., High-density, microsphere-based fiber optic DNA microarrays. Biosens Bioelectron. May 2003; 18(5-6):541-6.

Epstein, et al., Fluorescence-based fibre optic arrays: a universal platform for sensing. Chem Soc Rev. Jul. 2003; 32(4):203-14.

Ferguson et al., A fiber-optic DNA biosensor microarray for the analysis of gene expression. Nat Biotechnol. Dec. 1996; 14(13):1681-4.

Ferguson et al., High-density fiber-optic DNA random microsphere array. *Anal Chem.* Nov. 15, 2000; 72(22):5618-24.

Ferguson et al., Simultaneous monitoring of pH, $CO_2$ and $O_2$ using an optical imaging fiber. Analytica Chimica Acta. 1997; 340(1-3):123-131.

Fister et al., Counting single chromophore molecules for ultrasensitive analysis and separations on microchip devices. Analytical Chemistry. 1998; 70:431-437.

Fulton et al., Advanced multiplexed analysis with the FlowMetrix system. Clin Chem. Sep. 1997; 43(9):1749-56.

Furka et al., General method for rapid synthesis of multicomponent peptide mixtures. Int J Pept Protein Res. Jun. 1991;37(6):487-93.

Gebel, Molecule counting made easy. Anal Chem. Sep. 1, 2009; 7130-7131.

Giaever et al., Micromotion of mammalian cells measured electrically. Proc Natl Acad Sci U S A. Sep. 1, 1991;88(17):7896-900.

Gorris et al., Analytical chemistry on the femtoliter scale. Angew Chem Int Ed. 2010; 49:2-18.

Gorris et al., Mechanistic aspects of horseradish peroxidase elucidated through single-molecule studies. J Am Chem Soc. May 6, 2009; 131(17):6277-82.

Gorris et al., Optical-fiber bundles. FEBS J. Nov. 2007; 274(21):5462-70. Epub Oct. 12, 2007.

Gorris et al., Stochastic inhibitor release and binding from single-enzyme molecules. Proc Natl Acad Sci U S A. Nov. 6, 2007; 104(45):17680-5. Epub Oct. 26, 2007.

Härma et al., Europium nanoparticles and time-resolved fluorescence for ultrasensitive detection of prostate-specific antigen. Clin Chem. Mar. 2001; 47(3):561-8.

Härma et al., Miniature single-particle immunoassay for prostate-specific antigen in serum using recombinant Fab fragments. Clin Chem. Nov. 2000; 46(11):1755-61.

Härma et al., Zeptomole detection sensitivity of prostate-specific antigen in a rapid microtitre plate assay using time-resolved fluorescence. Luminescence. Nov.-Dec. 2000;15(6):351-5.

Hashida et al., Immune complex transfer enzyme immunoassay that is more sensitive and specific than western blotting for detection of antibody immunoglobulin G to human immunodeficiency virus type 1 in serum with recombinant pol and gag proteins as antigens. Clin Diagn Lab Immunol. Sep. 1995; 2(5):535-41.

Haugland, Handbook: A Guide to Fluorescent Probes and Labeling Technologies. Invitrogen, Eugene, OR. Molecular Probes, US. pp. 473-538.

He et al., Selective encapsulation of single cells and subcellular organelles into picoliter- and femtoliter-volume droplets. Anal Chem. Mar. 15, 2005; 77(6):1539-44.

Healey et al., Fiberoptic DNA sensor array capable of detecting point mutations. Anal Biochem. Sep. 5, 1997; 251(2):270-9.

Healey et al., Multianalyte biosensors on optical imaging bundles. Biosens Bioelectron. 1997; 12(6):521-9.

Healey et al., Photodeposition of micrometer-scale polymer patterns on optical imaging fibers. Science. Aug. 25, 1995; 269(5227):1078-80.

Hindson et al., High-throughput droplet digital PCR system for absolute quantitation of DNA copy number. Anal Chem. Nov. 15, 2011;83(22):8604-10. Epub Oct. 28, 2011.

Hirano et al., A novel method for DNA molecular counting. Nucleic Acids Symp Ser. 2000;(44):157-8.

Hirschfeld, Remote and in-situ analysis. Anal Chem. 1986; 324:618-624.

(56) References Cited

OTHER PUBLICATIONS

Hunsaker et al., Nucleic acid hybridization assays employing dA-tailed capture probes. II. Advanced multiple capture methods. Anal Biochem. Sep. 1989; 181(2):360-70.
Johnson et al., Identification of multiple analytes using an optical sensor array and pattern recognition neural networks. Analytical Chemistry. 1997; 69(22):4641-4648.
Joos, Quanterix Web Symposium: Immunoassays in Multiplex for Biomarker Discovery and Validation. Presentation. Feb. 27, 2013. 43 pages.
Kiss et al., High-throughput quantitative polymerase chain reaction in picoliter droplets. Anal Chem. Dec. 1, 2008;80(23):8975-81.
Kremsky et al., Immobilization of DNA via oligonucleotides containing an aldehyde or carboxylic acid group at the 5' terminus. Nucleic Acids Res. Apr. 10, 1987; 15(7):2891-909.
Kuang et al., Living bacterial cell array for genotoxin monitoring. Anal Chem. May 15, 2004; 76(10):2902-9.
Kuang et al., Monitoring "promiscuous" drug effects on single cells of multiple cell types. *Anal Biochem.* Oct. 15, 2005; 345(2):320-5.
Kuang et al., Simultaneously monitoring gene expression kinetics and genetic noise in single cells by optical well arrays. Anal Chem. Nov. 1, 2004; 76(21):6282-6.
Lafratta et al., Very high density sensing arrays. Chem Rev. Feb. 2008; 108(2):614-37. Epub Jan. 30, 2008.
Lee et al., A fiber-optic microarray biosensor using aptamers as receptors. Anal Biochem. Jun. 15, 2000; 282(1):142-6.
Li et al., Detection of single-molecule DNA hybridization using enzymatic amplification in an array of femtoliter-sized reaction vessels. J Am Chem Soc. Sep. 24, 2008; 130(38):12622-3. Epub Sep. 3, 2008.
Li et al., Molecule by molecule direct and quantitative counting of antibody-protein complexes in solution. Anal Chem. Aug. 1, 2004; 76(15):4446-51.
Lu et al., Single-molecule enzymatic dynamics. Science. Dec. 4, 1998; 282(5395):1877-82.
Luo et al., Single-molecule and ensemble fluorescence assays for a functionally important conformational change in T7 DNA polymerase. Proc Natl Acad Sci U S A. Jul. 31, 2007; 104(31):12610-5. Epub Jul. 18, 2007.
Melin et al., Microfluidic large-scale integration: the evolution of design rules for biological automation. Annu Rev Biophys Biomol Struct. 2007; 36:213-31.
Michael et al., Combined imaging and chemical sensing of fertilization-induced acid release from single sea urchin eggs. Anal Biochem. Sep. 10, 1999; 273(2):168-78.
Michael et al., Randomly ordered addressable high-density optical sensor arrays. Anal Chem. Apr. 1, 1998; 70(7):1242-8.
Monk et al., Fabrication of gold microtubes and microwires in high aspect ratio capillary arrays. J Am Chem Soc. Sep. 22, 2004; 126(37):11416-7.
Monk et al., Optical fiber-based biosensors. Anal Bioanal Chem. Aug. 2004; 379(7-8):931-45. Epub Jun. 23, 2004.
Monk et al., Progress toward the dermination of $Sr^{2+}$ in highly basic solutions using imagining optical fiber sensor arrays. J. Mater. Chem. 2005; 15:4361-4366.
Morrison et al., Nanoliter high throughput quantitative PCR. Nucleic Acids Res. 2006;34(18):e123. Epub Sep. 25, 2006.
Munkholm et al., Polymer modification of fiber optic chemical sensors as a method of enhancing fluroescence signal for pH measurement. Anal Chem. 1986; 58:1427-1430.
Nagai et al., High-throughput PCR in silicon based microchamber array. Biosens Bioelectron. Dec. 2001; 16(9-12):1015-9.
Nalefski et al., Single-molecule detection for femtomolar quantification of proteins in heterogeneous immunoassays. Clin Chem. Nov. 2006; 52(11):2172-5.
Nam et al., Nanoparticle-based bio-bar codes for the ultrasensitive detection of proteins. Science. Sep. 26, 2003;301(5641):1884-6.
Niemeyer et al., Combination of DNA-directed immobilization and immuno-PCR: very sensitive antigen detection by means of self-assembled DNA-protein conjugates. Nucleic Acids Res. Aug. 15, 2003; 31(16):e90, 7 pages.
Okrongly, Single Molecule Enzyme Detection and Application to Immunoassay: Implications for Personalized Medicine. Abstract and Presentation. ISE International Conference. May 4, 2010. 24 pages.
Panova et al., In situ fluorescence imaging of localized corrosion with a pH-sensitive imaging fiber. Anal Chem. Apr. 15, 1997; 69(8):1635-41.
Pantano et al., Analytical applications of optical imaging fibers. Anal Chem. Aug. 1, 1995; 67(15):481A-487A.
Pantano et al., Ordered nanowell arrays. Chemistry of Materials. 1996;8: 2832-2835.
Pantano et al., Toward a near-field optical array. Rev. Sci. Instrum. 1997; 68(3) 1357-1359.
Peterson et al., Fiber optic pH probe for physiological use. Anal Chem. May 1980; 52(6):864-9.
Qiu et al., Fluorescence single-molecule counting assays for high-sensitivity detection of cytokines and chemokines. Clin Chem. Nov. 2007; 53(11):2010-2.
Randle et al., Integrating molecular detection and response to create self-signalling antibodies. Biochem Biophys Res Commun. Nov. 12, 2004; 324(2):504-10.
Rissin et al., Attomolar detection of proteins in serum using single molecule enzyme-linked immunosorbent assays. Quanterix Corporation. Oak Ridge Conference, San Jose, CA. Poster. 2010. 1 page.
Rissin et al., Distinct and long-lived activity states of single enzyme molecules. J Am Chem Soc. Apr. 16, 2008; 130(15):5349-53. Epub Mar. 5, 2008.
Rissin et al., Duplexed sandwich immunoassays on a fiber-optic microarray. Anal Chim Acta. Mar. 30, 2006; 564(1):34-9. Epub Nov. 11, 2005.
Rissin et al., Immunoassays with broad dynamic ranges based on combining digital and digitally-enhanced analog detection of enzyme labels. Oak Ridge Conference. Poster 7 and Abstract. Apr. 14-15, 2011. 2 pages.
Rissin et al., Multiplexed single molecule immunoassays. Lab Chip. Aug. 7, 2013;13(15):2902-11. doi: 10.1039/c3lc50416f.
Rissin et al., Simultaneous detection of single molecules and singulated ensembles of molecules enables immunoassays with broad dynamic range. Anal Chem. Mar. 15, 2011;83(6):2279-85. Epub Feb. 23, 2011.
Rissin et al., Single-molecule enzyme-linked immunosorbent assay detects serum proteins at subfemtomolar concentrations. Nat Biotechnol. Jun. 2010; 28(6):595-9 and supplemental pages. Epub May 23, 2010.
Roeffaers et al., Single-molecule fluorescence spectroscopy in (bio)catalysis. Proc Natl Acad Sci U S A. Jul. 31, 2007; 104(31):12603-9. Epub Jul. 30, 2007.
Rondelez et al., Highly coupled ATP synthesis by F1-ATPase single molecules. Nature. Feb. 17, 2005; 433(7027):773-7.
Rondelez et al., Microfabricated arrays of femtoliter chambers allow single molecule enzymology. Nat Biotechnol. Mar. 2005; 23(3):361-5. Epub Feb. 20, 2005.
Rotman, Measurement of activity of single molecules of beta-D-galactosidase. Proc Natl Acad Sci U S A. Dec. 15, 1961; 47:1981-91.
Schauer et al., A cross-reactive, class-selective enzymatic array assay. J Am Chem Soc. Sep. 26, 2001; 123(38):9443-4.
Schmidinger, et al., Inhibitor and protein microarrays for activity-based recognition of lipolytic enzymes. Chembiochem. Mar. 2006; 7(3):527-34.
Schweitzer et al., Inaugural article: immunoassays with rolling circle DNA amplification: a versatile platform for ultrasensitive antigen detection. Proc Natl Acad Sci U S A. Aug. 29, 2000; 97(18):10113-9.
Seydack, Nanoparticle labels in immunosensing using optical detection methods. Biosens Bioelectron. Jun. 15, 2005; 20(12):2454-69. Epub Dec. 16, 2004.
Shen et al. High-throughput SNP genotyping on universal bead arrays. Mutat Res. Jun. 3, 2005;573(1-2):70-82.

(56) References Cited

OTHER PUBLICATIONS

Shepard et al., Array-based binary analysis for bacterial typing. Anal Chem. Jan. 1, 2005; 77(1):319-26.

Song et al., Detecting biological warfare agents. Emerg Infect Dis. Oct. 2005; 11(10):1629-32.

Song et al., Direct Detection of Bacterial DNA and viral RNA at Subfemtomolar Concentrations Using Single Molecule Arrays (Simoa). 2013 Oakridge Conference. Baltimore, MD. Abstract and Poster. 2013. 2 pages.

Song et al., Direct detection of bacterial genomic DNA at sub-femtomolar concentrations using single molecule arrays. Anal Chem. Feb. 5, 2013;85(3):1932-9. doi: 10.1021/ac303426b. Epub Jan. 18, 2013.

Song et al., Fiber-optic microsphere-based arrays for multiplexed biological warfare agent detection. Anal Chem. Feb. 15, 2006; 78(4):1023-33.

Song et al., Single molecule measurements of tumor necrosis factor α andinterleukin-6 in the plasma of patients with Crohn's disease. J. Immunol Methods Sep. 30, 2011;372(1-2):177-86. Epug Jul. 27, 2011.

Soukka et al., Supersensitive time-resolved immunofluorometric assay of free prostate-specific antigen with nanoparticle label technology. Clin Chem. 2001; 47(7):1269-78.

Stamou et al., Self-assembled microarrays of attoliter molecular vessels. Angew Chem Int Ed Engl. Nov. 24, 2003; 42(45):5580-3.

Steemers et al., Multi-analyte sensing: from site-selective deposition to randomly ordered addressable optical sensors. Microchimica Acta. 1999; 131:99-105.

Steemers et al., Screening unlabeled DNA targets with randomly ordered fiber-optic gene arrays. Nat Biotechnol. Jan. 2000; 18(1):91-4.

Stitzel et al., Array-to-array transfer of an artificial nose classifier. Anal Chem. Nov. 1, 2001; 73(21):5266-71. Epub Sep. 28, 2001.

Subbaraman, Detecting single cancer molecules. Technol Rev. Jun. 3, 2010. Last accessed at http://www.technologyreview.com/biomedicine/25462/ on Jan. 31, 2012. 2 pages.

Sykes et al., Quantitation of targets for PCR by use of limiting dilution. Biotechniques. 1992;13(3):444-9.

Szunerits et al., Aluminum surface corrosion and the mechanism of inhibitors using pH and metal ion selective imaging fiber bundles. Analytical Chemistry. 2002;74(4): 886-94.

Szunerits et al., Fabrication of an optoelectrochemical microring array. Analytical Chemistry. 2002; 74(7):1718-23.

Szunerits et al., Spatially resolved electrochemiluminescence on an array of electrode tips. Anal Chem. Sep. 1, 2003; 75(17):4382-8.

Szunerits et al., The use of optical fiber bundles combined with electrochemistry for chemical imaging. Chemphyschem. Feb. 17, 2003; 4(2):186-92. Epub Feb. 7, 2003.

Szurdoki et al., A duplexed microsphere-based fluorescent immunoassay. Anal Biochem. Apr. 15, 2001; 291(2):219-28.

Tam et al., An imaging fiber-based optical tweezer array for microparticle array assembly. Applied Physics Letters. 2004; 84(21):4289-4291.

Tam et al., Fabrication and optical characterization of imaging fiber-based nanoarrays. Talanta. Sep. 15, 2005; 67(3):498-502. Epub Jul. 27, 2005.

Tam et al., Parallel microparticle manipulation using an imaging fiber bundle-based optical tweezer array and a digital micromirror device. Applied Physics Letters. 2006; 89:194101/1-194101/3.

Tan et al., Monitoring the reactions of single enzyme molecules and single metal ions. Anal. Chem. 1997; 69:4242-4248.

Tanen et al., Development of an Ultrasensitive Digital Immunoassay on the Single Molecule Array (SimoaTM) Platform. 2014 AAPS Annual Meeting. San Diego, CA. Abstract and Poster. Nov. 2-6, 2014. 2 pages.

Taylor et al., Application of high-density optical microwell arrays in a live-cell biosensing system. Anal Biochem. Feb. 15, 2000; 278(2):132-42.

Tessler et al., Protein quantification in complex mixtures by solid phase single-molecule counting. Anal Chem. Sep. 1, 2009; 81(17):7141-8.

Thaxton et al., Nanoparticle-based bio-barcode assay redefines "undetectable" PSA and biochemical recurrence after radical prostatectomy. Proc Natl Acad Sci U S A. Nov. 3, 2009;106(44):18437-42. Epub Oct. 19, 2009.

Timmerman, Quanterix CEO sets sight on early detection of cancer, neurological diseases in the blood. Xconomy. Jan. 19, 2010. Last accessed at http://www.xconomy.com/boston/2010/01/19/quanterix-ceo-sets-sight-on-early-detection-of-cancer-neurological-diseases-in-the-blood/ on Jan. 31, 2012. 4 pages.

Todd et al., Ultrasensitive flow-based immunoassays using single-molecule counting. Clin Chem. Nov. 2007; 53(11):1990-5. Epub Sep. 21, 2007.

Tromberg et al., Development of antibody-based fiber-optic sensors for detection of a benzo[a]pyrene metabolite. Anal Chem. Sep. 15, 1988; 60(18):1901-8.

Ueberfeld et al., Reversible ratiometric probe for quantitative DNA measurements. Anal Chem. Feb. 15, 2004; 76(4):947-52. Epub Jan. 20, 2004.

Vo-Dinh et al., Phase-resolved fiber-optics fluoroimmunosensor. Applied Spectroscopy. 1990; 44(1):128-132.

Vogelstein et al., Digital PCR. Proc Natl Acad Sci U S A. Aug. 3, 1999;96(16):9236-41.

Walt et al., Biosensing with live cells using a high-density optical fiber array. Radiation Research. 2001; 156(4):442.

Walt et al., Microsensor arrays for saliva diagnostics. Ann N Y Acad Sci. Mar. 2007; 1098:389-400.

Walt et al., Optical sensor arrays for odor recognition. Biosens Bioelectron. Sep. 15, 1998; 13(6):697-9.

Walt et al., Ultrasensitive detection of proteins using single molecule arrays (SiMoA). Presented Mar. 1, 2010. Pittcon. Abstract and PowerPoint presentation. 32 pages.

Walt, An array of solutions, fiber arrays contribute to studies of individual cellular behavior and response. SPIE's oemagazine. 2005; 19-21.

Walt, Fiber optic array biosensors. Biotechniques. Nov. 2006; 41(5):529, 531, 533, 535 passim.

Walt, Fiber optic imaging sensors. Accounts of Chemical Research. 1998; 31:267-278.

Walt, Imaging optical sensor arrays. Curr Opin Chem Biol. Oct. 2002; 6(5):689-95.

Walt, Optical methods for single molecule detection and analysis. Anal Chem. Feb. 5, 2013;85(3):1258-63. doi: 10.1021/ac3027178. Epub Dec. 19, 2012.

Walt, Techview: molecular biology. Bead-based fiber-optic arrays. Science. Jan. 21, 2000; 287(5452):451-2.

Wang et al., Quantification of protein based on single-molecule counting by total internal reflection fluorescence microscopy with adsorption equilibrium. Anal Chim Acta. May 2, 2007; 590(1):104-9. Epub Mar. 15, 2007.

Warren et al., Transcription factor profiling in individual hematopoietic progenitors by digital RT-PCR. Proc Natl Acad Sci U S A. Nov. 21, 2006;103(47):17807-12. Epub Nov. 10, 2006.

Whitaker et al., Fiber-based single cell analysis of reporter gene expression in yeast two-hybrid systems. Anal Biochem. Jan. 1, 2007; 360(1):63-74. Epub Oct. 30, 2006.

Whitaker et al., Multianalyte single-cell analysis with multiple cell lines using a fiber-optic array. Anal Chem. Dec. 1, 2007; 79(23):9045-53. Epub Nov. 1, 2007.

White et al., An olfactory neuronal network for vapor recognition in an artificial nose. Biol Cybern. Apr. 1998; 78(4):245-51.

White et al., Rapid analyte recognition in a device based on optical sensors and the olfactory system. Analytical Chemistry. 1996; 68(13):2191-2202.

Wilson et al., Development of AccuPSA™, a novel digital immunoassay for sub-femtomolar measurement of PSA in post radical prostatectomy patients. AACR Molecular diagnostics in Cancer Therapeutic Development Abstract and Poster. 2011. 1 page.

Wilson et al., Fifth-generation digital immunoassay for prostate-specific antigen by single molecule array technology. Clin Chem. Dec. 2011;57(12):1712-21. Epub Oct. 13, 2011.

(56) References Cited

OTHER PUBLICATIONS

Wilson et al., Simoa™ HD-1: a fully automated digital immunoassay analyzer capable of single molecule counting, sub-femtomolar sensitivity, and multiplexing. 2014 AACC Meeting. Chicago, IL. Abstract and Poster. 2014. 2 pages.

Wilson, Serum Measurement of Hypoxia-Induced Amyloid Beta 1-42 Following Resuscitation from Cardiac Arrest. Abstract and Poster. American Academy of Neurology Annual Meeting. Apr. 9, 2011. 2 pages.

Wu et al., Development and preliminary clinical validation of a high sensitivity assay for cardiac troponin using a capillary flow (single molecule) fluorescence detector. Clin Chem. Nov. 2006; 52(11):2157-9.

Xie et al., Optical studies of single molecules at room temperature. Annu Rev Phys Chem. 1998; 49:441-80.

Xie et al., Single gold nanoparticles counter: an ultrasensitive detection platform for one-step homogeneous immunoassays and DNA hybridization assays. J Am Chem Soc. Sep. 9, 2009;131(35):12763-70.

Xue et al., Differences in the chemical reactivity of individual molecules of an enzyme. Nature. Feb. 23, 1995; 373(6516):681-3.

Yan et al., Analyzing polyubiquitin chains upon ubiquitin activating enzyme inhibition from cell culture & tumor lysates using the Quanterix's single molecule array (Simoa) technology. 2013 Society for the Laboratory Automation & Screening Annual Meeting. Orlando, FL. Abstract and Poster. 2013. 2 pages.

Young et al., Integrating high-content screening and ligand-target prediction to identify mechanism of action. Nat Chem Biol. Jan. 2008; 4(1):59-68. Epub Dec. 9, 2007.

\* cited by examiner

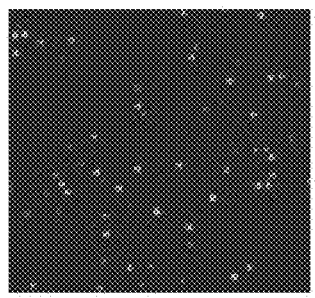 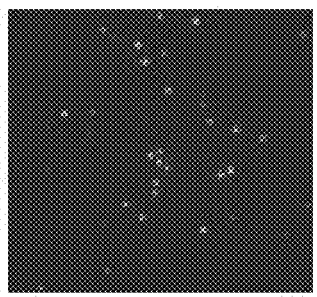 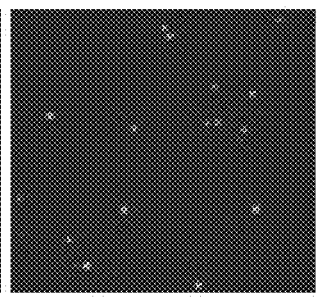
Fig. 4A          Fig. 4B          Fig. 4C
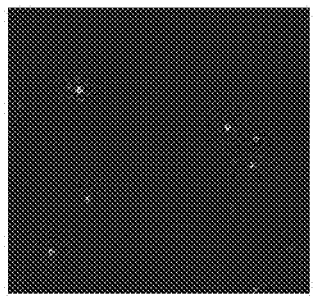 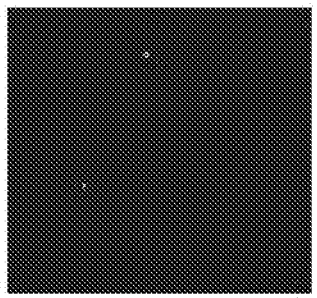 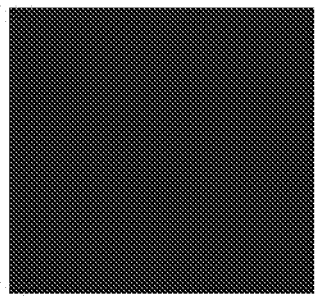
Fig. 4D          Fig. 4E          Fig. 4F

METHODS FOR DETERMINING THE CONCENTRATION OF AN ANALYTE IN SOLUTION

CROSS-REFERENCE TO RELATED APPLICATIONS

This application is a continuation of U.S. application Ser. No. 12/675,686, filed Apr. 4, 2011, now abandoned, which is a National Stage of International Application Serial No. PCT/US2007/019184, filed Aug. 30, 2007, each of which is incorporated herein by reference.

GOVERNMENT RIGHTS

The United States government may have certain rights in this invention pursuant to Contract No. N00014-01-1 awarded by the Department of Defense, Defense Advanced Research Projects Agency (DARPA) Office of Naval Research.

BACKGROUND

Methods that implement high-sensitivity and low-level analyte detection in conjunction with rapid and reproducible experimental protocols are the cornerstone of modern analytical measurements. Currently, most known techniques for quantifying low levels of analyte in a sample matrix use amplification procedures to increase the number of reporter molecules and thereby provide a measurable signal. These known processes include enzyrnelinked immunosorbent assays (ELISA) for amplifying the signal in antibody-based assays, as well as the polymerase chain reaction (PCR) for amplifying target DNA strands in DNA-based assays. A more sensitive but indirect protein target amplification technique, called immune-PCR (see Sano, T.; Smith, C. L.; Cantor, C. R. *Science* 1992, 258, 120-122), makes use of oligonucleotide markers, which can subsequently be amplified using PCR and detected using a DNA assay (see Nam, J. M.; Thaxton, C. S.; Mirkin, C. A. *Science* 2003, 301, I 884-1886; Niemeyer, C. M.; Adler, M.; Pignataro, B.; Lenhert, S.; Gao, S.; Chi, L. F.; Fuchs, H.; Blohm, D. *Nucleic Acids Research* 1999, 27, 4553-4561; and Zhou, H.; Fisher, R. J.; Papas, T. S. *Nucleic Acids Research* 1993, 21, 6038-6039). While the immuno-PCR method permits ultra low-level protein detection, it is a complex assay procedure, and can be prone to false-positive signal generation (see Niemeyer, C. M.; Adler, M.; Wacker, R. *Trends in Biotechnology* 2005, 23, 208-216).

One disadvantage of known methods for accurately quantifying the concentration of a particular analyte in solution is that they are all based on ensemble responses in which many analyte molecules give rise to the measured signal. Most detection schemes require that a large number of molecules are present in the ensemble for the aggregate signal to be above the detection threshold. This disadvantage limits the sensitivity of most detection techniques and the dynamic range (i.e., the range of concentrations that can be detected).

Therefore, there is a need in the art for an improved method and system of analyte detection. Specifically methods that detect and measure individual molecules rather than an ensemble of molecules would improve the sensitivity, dynamic range and accuracy of analyte detection. The invention described here divides the sample being analyzed into small samples in which only one or zero analyte molecules are present statistically. These analyte molecules are then detected and counted in a digital fashion to determine the concentration of analyte.

BRIEF SUMMARY OF THE INVENTION

The invention relates to methods, systems and devices for measuring the concentration of an analyte or analytes in a fluid sample. The methods can be performed using a variety of assay platforms, reagents, detectable labels, reaction conditions, and detection systems which are described in detail herein.

In one aspect, the invention provides a method of determining the concentration of an analyte in a fluid sample. The method comprises the steps of: (a) partitioning at least a portion of the analyte molecules in the fluid sample across a plurality of reaction vessels so that a statistically significant fraction of the reaction vessels contain analyte and a statistically significant fraction of the reaction vessels contain no analyte; (b) determining the presence or absence of the analyte in each reaction vessel to identify the number of reaction vessels that contain analyte and/or to identify the number of reaction vessels that contain no analyte; and (c) determining the concentration of the analyte in the fluid sample from the number of reaction vessels that contain the analyte.

In this method, at least 95%, optionally 90%, optionally 80%, optionally 40%, optionally 5%, of the reaction vessels contain no analyte. Depending upon the reaction conditions chosen and the number of wells that contain one or more molecules of analyte, the concentration of the analyte in the fluid sample can be determined by either Poisson distribution analysis or Gaussian distribution analysis of the number of reaction vessels that contain the analyte.

The reaction vessels can be adapted to capture the analyte of interest. For example, depending upon the assay format chosen, the reaction vessel can comprise a microwell and an optional sealing component that connects and seals fluid within the microwell. Accordingly, a capture component for capturing the analyte can be immobilized on a sample contacting surface of the microwell or a sample contacting surface of the sealing component. Alternatively, the capture component can be immobilized on the surface of a particle disposed within the reaction vessel.

The methods preferably are performed using at least 1000 reaction vessels. More specifically, under certain circumstances the methods are performed simultaneously using from about 10,000 to about 200,000 different reaction vessels, more preferably from about 50,000 to about 100,000 different reaction vessels. In addition, in certain embodiments, at least a portion of the reaction vessel is defined by a distal end of an optical fiber. As a result, light from a light source, for example, a laser or lamp, can be transmitted along the optical fiber to the reaction vessel located at the distal end of the optical fiber. Thereupon, depending up the label chosen for a given assay, photoexcitation of the label produces a signal, which then can be detected by a suitable detector.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 4a, FIG. 4b, FIG. 4c, FIG. 4d, FIG. 4e, and FIG. 4f are photographs depicting experiments according to one embodiment of the present invention in which β-galactosidase hydrolyzes RDG to form resorufin. More specifically, each of these figures depicts a different sample having a different concentration of SβG. The concentrations were: (a) 128 amol, (b) 51 amol, (c) 25 amol, (d) 7.5 amol, and (e) 2.6 amol, and (f) was the control.

FIG. 7a is a microscopic photograph of a solution of $Ru(bpy)_3Cl_2$ enclosed in the array of reaction vessels. FIG. 7b is a microscopic photograph of a small octagonal portion of the reaction vessels that have been photobleached with UV light. FIG. 7c is a microscopic photograph of FIG. 7b taken 60 minutes later.

FIG. 8a is a microscopic photograph of a background image of a portion of an array of reaction vessels. FIG. 8b is a microscopic photograph of an image taken of a portion of a 1:5 ratio of enzyme-to-reaction vessel assay. FIG. 8c is a microscopic photograph of a 1:80 ratio of enzyme-to-reaction vessel assay.

DETAILED DESCRIPTION

Figures 1A, 1B, 1C, 1D:
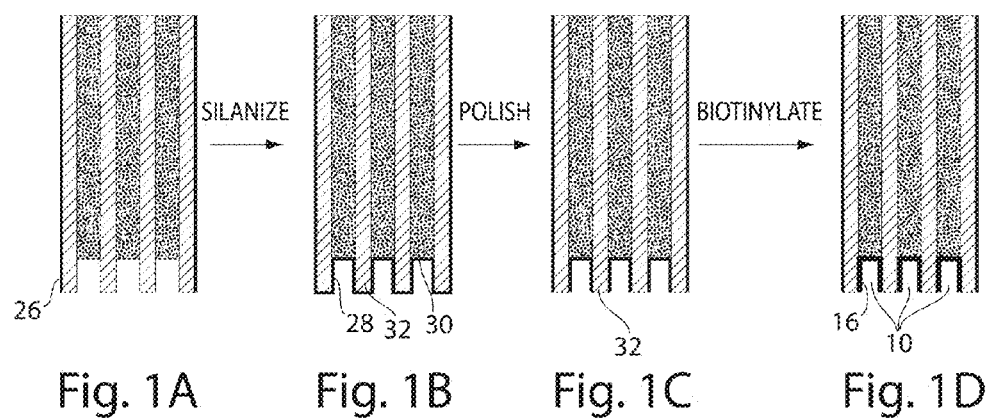
FIG. 1a, FIG. 1b, FIG. 1c, and FIG. 1d are side view cross-section schematics representing etched fiber optica bundle that form an array of microwells, according to one embodiment of the present invention.

The present invention relates to methods, systems, and devices for the detection and quantification of an analyte or analytes in a sample. It is contemplated that the methods described herein can be performed in a number of different formats using a variety of different detectable labels, reagents, reaction conditions, and detection systems.

In one aspect, the invention provides a method of determining the concentration of an analyte in a fluid sample to be tested. The method comprises the steps of: (a) partitioning at least a portion of the analyte molecules in the fluid sample across a plurality of reaction vessels so that a statistically significant fraction of the reaction vessels contain analyte and a statistically significant fraction of the reaction vessels contain no analyte; (b) determining the presence or absence of the analyte in each reaction vessel to identify the number of reaction vessels that contain analyte and/or to identify the number of reaction vessels that contain no analyte; and (c) determining the concentration of the analyte in the fluid sample from the number of reaction vessels that contain the analyte.

In another aspect, the invention provides a method of determining the concentration of an analyte in a fluid sample to be tested. The method comprises the steps of: (a) exposing the fluid sample to a plurality of reaction vessels under conditions so that analyte is captured in a statistically significant fraction of the reaction vessels, wherein each reaction vessel comprises a microwell and an optional sealing component and each reaction vessel defines a binding surface that has a capture component immobilized thereon; (b) determining the presence or absence of the analyte in each reaction vessel so as to identify the number of reaction vessels that contain captured analyte and/or the number of reaction vessels that do not contain captured analyte; and (c) determining the concentration of the analyte in the fluid sample to be tested from the number of reaction vessels that contain and/or do not contain the analyte.

In another aspect, the invention provides a method of determining the concentration of an analyte in a fluid sample to be tested. The method comprises the steps of: (a) partitioning at least a portion of the analyte molecules in the fluid sample into a plurality of reaction vessels, so that, for substantially all of the reaction vessels, each reaction vessel contains either no analyte or a single molecule of the analyte; (b) determining the presence or absence of the analyte in each reaction vessel to provide a number of the reaction vessels that contain the analyte; and (c) determining the concentration of the analyte in the fluid sample from the number of reaction vessels that contain the analyte.

In another aspect, the invention provides a method of determining the concentration of an analyte in a fluid sample to be tested. The method comprises the steps of: (a) partitioning the sample to be tested into a plurality of second, smaller fluid samples of equal volume so that a statistically significant fraction of the second, smaller fluid samples contain either a single molecule of the analyte or no analyte; (b) determining the presence or absence of the analyte in each of the second samples so as to identify the number of second samples that contain the analyte; and (c) determining the concentration of the analyte in the sample to be tested from the number of second samples that contain the analyte.

It is understood that the foregoing methods can be performed using a number of different assay formats, different reaction conditions, detectable labels and detection systems. In one embodiment, for example, the invention permits the detection and/or quantification of analytes using arrays of micron- to nanoscale-sized reaction vessels. In one approach, the reaction vessels contain capture components that capture the analyte within the reaction vessel. In such an approach, an array of reaction vessels containing an immobilized capture component is contacted with a sample containing at least one analyte. Following capture of the analyte, depending upon what label is used, the presence of analyte can be detected directly or indirectly.

The direct approach can include, for example, the situation where the analyte is an enzyme. In this case, a chromogenic, fluorogenic, or chemoluminescent enzymatic substrate is included in the reaction mixture and the enzymatic activity of the analyte produces a detectable product. The indirect approach can include, for example, the situation where the analyte does not have intrinsic enzymatic activity and a label is permitted to bind, for example, via a secondary binding ligand, to the analyte. For example, a detectable label conjugated to a secondary binding ligand (for example, a capture component different from the one used to capture the analyte) is added to the captured analyte under conditions to permit the labeled secondary binding ligand to bind to the immobilized analyte. Thereafter, the presence of the label can then be determined to provide an indication of whether the analyte is present in the reaction vessel. It is understood that a variety of different labels, as will be discussed in more detail below, may be used in the practice of the invention. To the extent that an enzymatic label is employed, an enzymatic substrate can be added to the reaction vessel whereupon the enzyme converts the substrate into a chromogenic, fluorogenic, or chemoluminescent detectable product to permit the detection of the analyte. The number or percentage of reaction vessels with captured analytes can be used to calculate the amount of analyte in the sample using a binary readout method.

Similarly, it is understood that in certain assay formats, some or all of the reaction vessels can be defined on a planar support rather than within the recesses of an array of microwells. For example, the sample containing analyte is divided into a plurality of second, smaller fluid samples of equal volume. The second fluid samples then are applied as droplets to the surface of a planar binding surface to create an array of droplets. Each droplet can be applied to a region of the planar binding surface having a capture component immobilized thereon. The samples then are incubated to permit the analyte to bind to the capture component immobilized on the planar binding surface. Afterwards, depending upon the label being employed, the presence of the analyte can be determined directly or indirectly so as to permit the identification of the number of fluid samples that contain the analyte and the number of fluid samples that do not contain the analyte. In certain embodiments, for example, when the label is an enzymatic label, an enzymatic substrate can be added to the surface of the planar binding surface, and the various regions containing the capture component (in the presence or absence of analyte). The planar binding substrate then is sealed against an array of microwells to form an array of reaction vessels to permit the development of a detectable product in each reaction vessel. From the number of reaction vessels containing the analyte in the array of reaction vessels it is possible to determine the concentration of analyte in the test solution.

In one embodiment, the present invention uses an array of micron- to nanoscale-sized reaction vessels specifically functionalized with capture components and capable of capturing analyte molecules. The ability to capture the analyte allows the use of washing steps and indirect assays, as outlined below. In one embodiment, the label used to detect the captured analyte is an enzyme. Once captured in individual reaction vessels, the enzyme catalyzes the production of a sufficient number of chromogenic, fluorogenic, or chemoluminescent product molecules to generate a detectable signal. In accordance with one embodiment relating to samples having low analyte concentrations, only a portion of the reaction vessels capture an analyte molecule, thereby enabling a binary readout of analyte concentration from the array of reaction vessels. The direct enzymatic amplification in the method and system of the present invention allows for direct amplification of a detectable signal.

The present invention allows for detection of low concentrations of analytes, such as proteins. At low concentrations, a statistically significant number of reaction vessels contain zero, one, or several molecules of the target analyte. By observing the presence or absence of a detectable label present in each reaction vessel, a binary readout method can be used to identify the number of reaction vessels that contain one or more molecules of the analyte. As a result, the percentage of reaction vessels occupied by analyte can be used to calculate the original bulk concentration of the analyte in the sample of interest. The following sections discuss exemplary arrays of reaction vessels, capture components, analytes that can be detected by the invention, detectable labels and signal detection protocols, assay methods, and exemplary uses of the invention.

I. Arrays of Reaction Vessels

The present invention utilizes an array of reaction vessels to carry out steps in an assay utilized to determine the concentration of an analyte of interest. The purpose of the array of reaction vessels is to allow a reaction volume to be partitioned into a plurality of discrete reaction volumes during one or more steps in an assay. By "array" herein is meant a plurality of similar reaction vessels.

The reaction vessels may all have the same volume or may be of differing, but known volumes. The volume of each individual reaction vessel can range from attoliters to nanoliters depending upon the analyte of interest and the expected concentration of that analyte in a solution. In one embodiment, the size of the reaction vessel may be selected such that at the concentration of interest between zero and ten molecules of the analyte of interest would be expected to be found in each reaction vessel. In accordance with one embodiment of the present invention, the reaction vessels have a volume ranging from about 10 attoliters to about 50 picoliters. Alternatively, the reaction vessels range in size from about 1 picoliter to about 50 picoliters. In a further alternative, the reaction vessels range in size from about 1 femtoliter to about 1 picoliter. In a further alternative, the reaction vessels range from about 30 femtoliters to about 60 femtoliters.

The number of reaction vessels in the array will depend on the composition and end use of the array. Arrays containing from about 2 to many billions of reaction vessels can be made by utilizing a variety of techniques and materials. Increasing the number of reaction vessels in the array can be used to increase the dynamic range of an assay or to allow multiple samples or multiple analytes to be assayed in parallel. Generally, the array will comprise between one thousand and one million reaction vessels per sample to be analyzed. Arrays used to simultaneously analyze multiple samples will generally contain between 10 thousand and 10 billion reaction vessels.

The array of reaction vessels may be arranged on a planar structure or in some 3 dimensional arrangement. They may be in a regular design or randomly distributed. A preferred embodiment utilizes a regular pattern of sites on a planar structure such that the sites may be addressed in the X-Y coordinate plane.

The reaction vessels can be formed in a solid material. As will be appreciated by those in the art, the number of possible materials are very large, and include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, composite materials, ceramics, and plastic resins, silica or silica-based materials including silicon and modified silicon, carbon, metals, inorganic glasses, plastics, optical fiber bundles, and a variety of other polymers. In general, the substrates allow optical detection and do not appreciably fluoresce.

The reaction vessels can also be formed in a liquid provided that the confining liquid does not mix with the liquid defining the reaction vessel, and that the reaction vessel is stable. Examples of suitable liquids for confining aqueous reactions include, but are not limited to, water-in-oil emulsions, extruded lipid aggregates, stable suspensions of lipids, liquid-crystal aggregates, micelles in water, inverted micelles in oil, and suspensions of cells, bacteria and viruses.

Individual reaction vessels may contain a binding surface. The binding surface may be all or a portion of the interior surface of the reaction vessel or may be on the surface of something that is confined within the reaction vessel such as a bead, or a particle (for example, a micro-particle or a nanoparticle).

In one embodiment, the array of reaction vessels is formed by mating an array of microwells with a sealing component. Microwells are small depressions in a first surface of a supporting material. The microwells may be formed as is generally known in the art using a variety of techniques, including, but not limited to, photolithography, stamping techniques, molding techniques and microetching techniques. As will be appreciated by those in the art, the technique used will depend on the composition and shape of the supporting material. The sealing component has a second surface with the same topology as the first surface that when brought into contact with the first surface creates an array of sealed reaction vessels. Either the first surface or the second surface may be fabricated from a compliant material to aid in sealing. Either or both surfaces may be hydrophobic or contain hydrophobic regions to minimize leakage from the microreactors.

In another embodiment, the array of reaction vessels is formed utilizing a microfluidic device that contains channels and valves that can be closed to isolate discrete reaction volumes.

In one preferred embodiment, an array of reaction vessels is formed creating microwells on the distal end of a fiber optic bundle and utilizing a planar compliant surface as a sealing component. Such an array of reaction vessels can be made as follows. First, an array of microwells are etched into the distal end of a polished fiber optic bundle. The diameter of the optical fibers and the depth of the etch can be varied to create microwells of the desired volume. The etching process creates the microwells in the core material of the individual glass fibers in the bundle such that each well is aligned with a single fiber and isolated from adjacent wells by the slower etching cladding material. One advantage of the fiber optic array format is that it can produce thousands to millions of reaction vessels without the need for complicated microfabrication procedures and provides the ability to observe many reaction vessels simultaneously.

Each microwell is aligned with an optical fiber in the bundle so that the fiber optic bundle can carry both excitation and emission light to and from the wells, enabling remote interrogation of the well contents. Further, an array of optical fibers provides the capability for simultaneous excitation of molecules in adjacent vessels, without signal "cross-talk" between fibers. That is, excitation light transmitted in one fiber does not escape to a neighboring fiber. In one aspect of the present invention, the physical alterations can be made as taught in U.S. Pat. Nos. 6,023,540, 6,327,410, and 6,858,394, which are each incorporated by reference herein in their entirety. Either the surface of the glass microwells, the surface of the sealing component, or particles can be functionalized to create a binding surface.

Alternatively, the equivalent structures can be fabricated using other methods that do not comprise the ends of an optical fiber bundle. For example, the array may be a spotted, printed or photolithographic substrate known in the art; see for example WO 95/25116; WO 95/35505; PCT US98/09163; U.S. Pat. Nos. 5,700,637; 5,807,522 and 5,445,934; and U.S. Ser. Nos. 08/851,203 and 09/187,289, all of which are expressly incorporated by reference.

II. Capture Components

During practice of the invention, the binding surfaces within the reaction vessels (including microwells defined in fiber optical bundles) incorporate at least one capture component. A capture component (also commonly referred to as a "capture binding ligand," "binding ligand," "capture binding species," or "capture probe") is any molecule, compound, or solid support modification that can be used to probe for, attach, bind or otherwise capture an analyte disposed upon a solid support, such that the analyte is immobilized during the assay. Generally, the capture component allows the attachment of an analyte to a solid support (that is, the surface of the microwells, the sealing component or nanoparticle) for the purposes of detection, quantification, or other analysis.

As will be appreciated by those in the art, the composition of the capture component will depend on the composition of the analyte. Capture components for a wide variety of analytes are known or can be readily found using known techniques. For example, when the analyte is a protein, the capture components include proteins (particularly including antibodies or fragments thereof (FAbs, etc.)) or small molecules. Preferred capture component proteins include peptides. For example, when the analyte is an enzyme, suitable capture components include substrates and inhibitors. Antigen-antibody pairs, receptor-ligands, and carbohydrates and their binding partners are also suitable analyte-capture component pairs. In addition, when the analyte is a single-stranded nucleic acid, the capture component may be a complementary nucleic acid. Similarly, the analyte may be a nucleic acid binding protein and the capture component is either single-stranded or double-stranded nucleic acid; alternatively, the capture component may be a nucleic acid-binding protein when the analyte is a single or double-stranded nucleic acid. Alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for capturing virtually any analyte. As will be appreciated by those in the art, any two molecules that will associate may be used, either as an analyte or as the capture component. Similarly, when the analyte is a carbohydrate, suitable capture components include antibodies and lectins. It is understood that there is a wide body of literature relating to the development of capture components based on combinatorial chemistry methods.

Suitable analyte/capture component pairs include, but are not limited to, antibodies/antigens, receptors/ligands, proteins/nucleic acid, enzymes/substrates and/or inhibitors, carbohydrates (including glycoproteins and glycolipids)/lectins, proteins/proteins, proteins/small molecules; and carbohydrates and their binding partners are also suitable analyte-capture component pairs. These may be wild-type or derivative sequences. According to one embodiment, the capture components are portions (particularly the extracellular portions) of cell surface receptors that are known to multimerize, such as the growth hormone receptor, glucose transporters (particularly GLUT 4 receptor), and T-cell receptors.

In a preferred embodiment, the capture component is attached to a binding surface (for example, the surface of a microwell) via an "attachment component" (also referred to herein as an "attachment linker"). An "attachment component," as used herein, is defined as any component, functionalization, or modification of the binding surface that results in the attachment of the capture component, and can include bonds and/or linkers. Alternatively, the capture component may utilize a capture extender component. In this embodiment, the capture component comprises a first portion that will bind the analyte and a second portion that can be used for attachment to the binding surface.

This attachment component can also provide a protective layer that screens the binding surface, such as the glass of a fiber optic bundle, from the assay solution. As a result, the attachment component minimizes non-specific attachment of non-target molecules to the binding surface during the assay and detection that could lead to undesired fluorescent wells and false positive signals.

The method of attachment of the capture component to the attachment component will generally be done as is known in the art, and will depend on the composition of the attachment component and the capture component. In general, the capture components are attached to the attachment component through the use of functional groups on each that can then be used for attachment. According to one embodiment, the functional group is a chemical functionality. That is, the binding surface is derivatized such that a chemical functionality is presented at the binding surface. Preferred functional groups for attachment are amino groups, carboxy groups, epoxide groups, maleimide groups, oxo groups and thiol groups. These functional groups can be attached, either directly or through the use of a linker, the combination of which is sometimes referred to herein as a "cross-linker." Linkers are known in the art; for example, homo- or heterobifunctional linkers as are well known (see 1994 Pierce Chemical. Company catalog, technical section on cross-linkers, pages 155-200, incorporated herein by reference). Preferred linkers include, but are not limited to, alkyl groups (including substituted alkyl groups and alkyl groups containing heteroatom moieties), with short alkyl groups, esters, amide, amine, epoxy groups and ethylene glycol and derivatives being preferred. Linkers may also be a sulfone group, forming sulfonamide.

According to one embodiment, the functional group is a light-activated functional group. That is, the functional group can be activated by light to attach to the capture component or to the attachment component. One example is the PhotoLink™ technology available from SurModics, Inc. in Eden Prairie, Minn.

Alternatively, the attachment component is added without covalently modifying the binding surface. That is, the attachment component can be added to the binding surface by using a molecule that has both a functional group and a group that has binding affinity for the binding surface. Alternatively, the attachment component is any protein capable of binding or sticking to the binding surface. In a further alternative, the attachment component is any molecule capable of binding or sticking to the vessel surface. In one example, the attachment component is serum albumin with free amine groups on its surface. A crosslinker can then be added to attach the amine groups of the albumin to the capture component.

According to one embodiment in which the capture component is a chemical crosslinker, the analyte is captured on the binding surface using chemical crosslinking in the following manner. First, the binding surface is derivatized with a functional group, such as, an amine group. Next, a crosslinker and the analyte are placed in contact with the binding surface such that one end of the crosslinker attaches to the amine group and the analyte attaches to the other end of the crosslinker. In an alternative embodiment described in further detail below in which the analyte is not an enzyme, a label having an enzymatic component can also be attached to the analyte.

In this way, capture components comprising proteins, lectins, nucleic acids, small organic molecules, carbohydrates can be added.

One embodiment utilizes proteinaceous capture components. As is known in the art, any number of techniques may be used to attach a proteinaceous capture component. "Protein" in this context includes proteins, polypeptides, peptides, including, for example, enzymes and antibodies. A wide variety of techniques are known to add moieties to proteins. One preferred method is outlined in U.S. Pat. No. 5,620,850, hereby incorporated by reference in its entirety. The attachment of proteins to surfaces is known; see also Heller, Acc. Chem. Res. 23:128 (1990), and related work.

An alternative embodiment utilizes nucleic acids as the capture component, for example for when the analyte is a nucleic acid or a nucleic acid binding protein, or when the nucleic acid serves as an aptamer for binding a protein, as is well known in the art.

According to one embodiment, each binding surface presents a plurality of capture component molecules. The plurality of capture component molecules, in one aspect of the invention, are distributed on the binding surface like a "lawn." Alternatively, the capture components are distributed in any known fashion.

The binding between the capture component and the analyte, in accordance with one embodiment, is specific and the capture component is part of a binding pair. That is, the capture component is a target-specific capture component that specifically binds with or has specificity for the analyte. More specifically, the capture component binds specifically and directly to the analyte. By "specifically bind" or "binding specificity" herein is meant that the capture component binds the analyte with specificity sufficient to differentiate between the analyte and other components or contaminants of the test sample. For example, the capture component according to one embodiment is an antibody that binds specifically to some portion of the analyte. The antibody, according to one embodiment, can be any antibody capable of binding specifically to an analyte. For example, appropriate antibodies include, but are not limited to, monoclonal antibodies, bispecific antibodies, minibodies, domain antibodies, synthetic antibodies (sometimes referred to as "antibody mimetics"), chimeric antibodies, humanized antibodies, antibody fusions (sometimes referred to as "antibody conjugates"), and fragments of each, respectively.

However, as will be appreciated by those in the art, it is possible to detect analytes using binding that is not highly specific. For example, the systems may use different capture components such as, for example, a panel of different binding ligands, and detection of any particular analyte is via its "signature" of binding to this panel of binding ligands, similar to the manner in which "electronic noses" work. This finds particular utility in the detection of chemical analytes. The binding affinity between analyte and capture component should be sufficient to remain bound under the conditions of the assay, including wash steps to remove non-specific binding. In some embodiments, for example in the detection of certain biomolecules, the binding constants of the analyte to the capture component will be at least about $10^4$-$10^6$ $M^{-1}$, with at least about $10^5$ to $10^9$ $M^{-1}$ being preferred and at least about $10^7$-$10^9$ $M^{-1}$ being particularly preferred.

According to one embodiment in which the analyte is a cell, including, for example, bacterial cells, the capture component can be an adhesin receptor molecule. In use, the adhesin receptor molecule binds with a surface protein called an adhesin on the extracellular surface of the target cell, thereby immobilizing or capturing the cell. Alternatively, in embodiments in which the analyte is another type of cell (a non-bacterial cell), the capture component is an appropriate cell surface receptor that binds the analyte cell. In a further embodiment in which the analyte is a cell, the capture component is fibronectin. For example, fibronectin can be used when the analyte is a nerve cell.

Alternatively, the capture component is a non-specific capture component. That is, the capture component does not bind specifically to an analyte, but rather binds to a corresponding binding partner associated with or attached to the analyte. For example, the non-specific capture component according to one embodiment is a chemical cross-linker as described above. According to one embodiment, every peptide molecule in a sample of analyte can attach to the chemical cross-linker. In one example of a non-specific capture component according to one embodiment, the capture component is streptavidin, which binds with high affinity to biotin, and thus captures any molecule to which biotin has been attached. Alternatively, the capture component is biotin, and streptavidin is attached to or associated with the analyte such that the analyte can be captured by the biotin.

According to one embodiment, the capture component is added to the binding surface in the following manner. First, an array of microwells on the distal end of a fiber optic bundle are prepared for attachment of the capture component(s). That is, the binding surface of the microwells are modified or an attachment component is added to the binding surface of the microwells such that the capture component(s) attach to the binding surface of the microwells. In one embodiment, the binding surface of the microwells are derivatized with a chemical functionality as described above. Next, the capture component is added.

One example of capture component attachment is depicted in FIG. 1, in which binding surface of an array of microwells of the present invention are functionalized with biotin. As shown in FIG. 1a, the array of microwells of the present invention in this example is formed at the distal end of a fiber optic bundle 26. To attach the capture component, the binding surface of the microwells are first modified with an attachment component 28, which in this example is an aminopropyl silane 28 that is bound to both the core 30 and cladding 32 surfaces of the distal end of the fiber bundle 26, as shown in FIG. 1b. The modification with aminopropyl silane is effective in this example because NHS-biotin attaches to an amino-silanized binding surface 28. However, since the capture component should be present only within the microwells, the external surfaces of the fiber optic bundle, such as the external surfaces of the cladding 32, should not be silanized. That is, the silanization must be removed from the external cladding surface 32 to avoid biotin attachment. In this example as shown in FIG. 1c, the silanization 28 was removed from the external cladding layer 32 by polishing the amino-silanized fiber optical bundle for 10 seconds with 0.3 μm lapping film, thereby removing the top amino-silanized cladding layer.

After the attachment component 28 has been added to the binding surface of the microwells, the capture component can be attached. The capture component can be biotin. For example, with respect to FIG. 1d, biotin succinimidyl ester is attached to the amino groups 28 on the binding surfaces of the microwells 10.

Figure 1E:
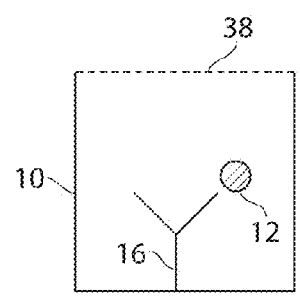
FIG. 1e, FIG. 1f, and FIG. 1g are side view cross-section schematics depicting the localization of a capture component within a microwell.
Figure 1F:
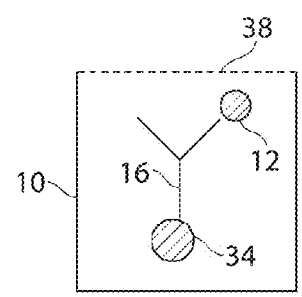
Figure 1G:
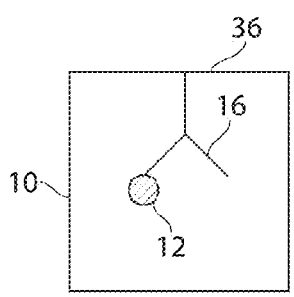

Examples of capture components within the microwell 10 are depicted in FIGS. 1e-g. A capture component 16 may be localized on the surface of the microwell 10, which may contain an optional seal 38 (FIG. 1e), on a microparticle 34 contained within the microwell 10, which may contain an optional seal 38 (FIG. 1f), and/or on the seal 36 of the microwell 10 (FIG. 1g).

Figure 9:
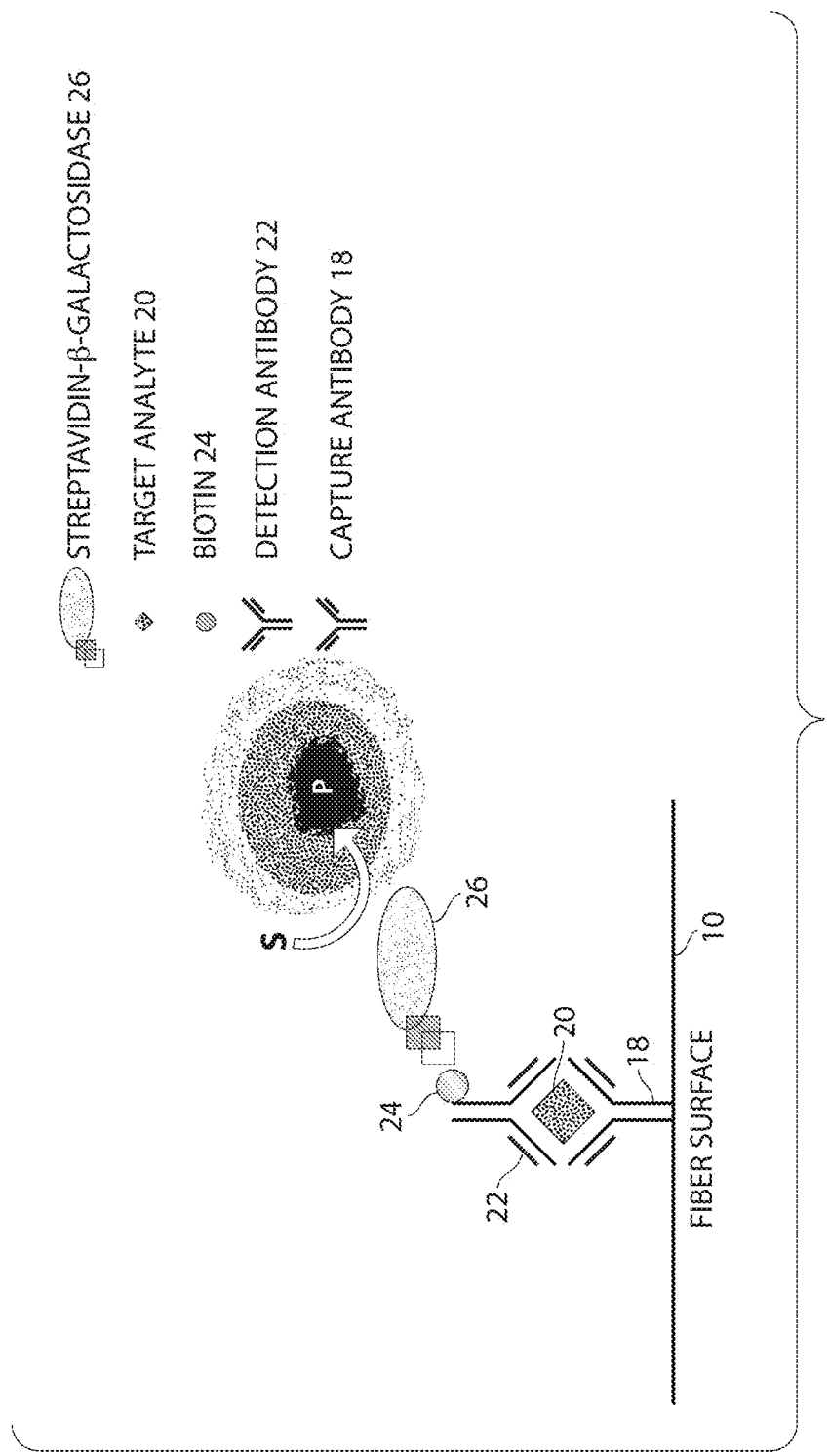
FIG. 9 is a schematic representation of an assay format used in Example 3.

Another example of a capture component attachment is depicted in FIG. 9, in which the binding surface of the microwells of the present invention are functionalized with an antibody to the analyte of interest. As shown in FIG. 9, which is discussed in more detail in Example 3, an array of microwells is formed at the distal end of a fiber optic bundle 10. To attach the antibody capture component 16, the binding surface of the microwells are first modified with an attachment component, which in Example 3 is aminopropyl silane that has then been reacted with the homobifunctional cross-linker N,N'-disuccinimidyl carbonate. This surface then reacts with lysine groups on the antibody to present the capture component at the binding surface of the microwells.

III. Analytes

As discussed herein, the array of reaction vessels in the present invention provides for detection, quantification, and further analysis of analytes. By "analyte" or grammatical equivalents herein is meant any atom, molecule, ion, molecular ion, compound, particle, cell, or virus to be either detected or evaluated.

According to one embodiment, the analyte is an enzyme. For example, the enzyme can be an enzyme from any of the following enzyme classifications: oxidoreductases, transferases, kinases, hydrolases, lyases, isomerases, and ligases. Thus, appropriate enzymes include, but are not limited to, polymerases, cathepsins, calpains, amino-transferases such as, for example, AST and ALT, proteases such as, for example, caspases, nucleotide cyclases, transferases, lipases, enzymes associated with heart attacks, and the like. When the system of the present invention is used to detect viral or bacterial targets, appropriate enzymes include viral or bacterial polymerases and other such enzymes, including viral or bacterial proteases.

Alternatively, the analyte has an enzymatic component. For example, the analyte can be a cell having an enzyme or enzymatic component present on its extracellular surface. Alternatively, the analyte is a cell having no enzymatic component on its surface. Such a cell is typically identified using an indirect assaying method described below such as a "sandwich" assay.

In accordance with another embodiment, the analyte is not an enzyme. As will be appreciated by those in the art, a large number of analytes may be used in the present invention; basically, any analyte can be used which binds a capture component and/or a secondary binding ligand. As will be explained in further detail below, these analytes are typically identified using an indirect assay such as a "sandwich" assay. As mentioned above, one suitable analyte is a cell. In addition, suitable analytes include organic and inorganic molecules, including biomolecules. In a preferred embodiment, the analyte is a protein. As will be appreciated by those in the art, there are a large number of possible proteinaceous analytes that may be detected or evaluated for binding partners using the present invention. In addition to enzymes as discussed above, suitable protein analytes include, but are not limited to, (1) immunoglobulins; (2) hormones and cytokines (many of which serve as ligands for cellular receptors); (3) cancer markers; and (4) other proteins.

According to one embodiment in which the analyte is not an enzyme and a sandwich assay is performed as described in further detail below, the enzymatic label as described in further detail below can be beta-galactosidase. Alternatively, the enzyme label can be, but is not limited to, alkaline phosphatase or horseradish peroxidase.

Further suitable analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc.

In certain embodiments, the analyte may be a post-translationally modified protein (e.g., phosphorylation, methylation, glycosylation) and the capture component may be an antibody specific to a post-translational modification. Modified proteins may be captured with a multiplicity of specific antibodies and then visualized with use of a specific-secondary antibody to a post-translational modification. Alternatively, modified proteins may be captured with an antibody specific for a post-translational modification and then visualized with specific antibodies to each modified protein.

In another embodiment, the analyte is a nucleic acid. A nucleic acid may be captured with a capture nucleic acid (e.g., an oligonucleotide) and then visualized with a different specifically labeled oligonucleotide.

IV. Detectable Labels and Signal Detection

It is understood that a variety of detectable labels can be used in the practice of the methods described herein. For example, it is understood that a variety of colored labels (for example, metallic nanoparticles (for example, gold nanoparticles), semiconductor nanoparticles, semiconductor nanocrystals (for example, quantum dots), spectroscopic labels (for example, fluorescent labels), radiolabels, and enzymatic labels may be used in the practice of the invention.

Depending upon the particular assay format, the detectable labels are indirectly attached to the analyte after it has been captured by the capture component, for example, via a secondary binding ligand that is conjugated to a detectable label and binds to the captured analyte. Once the label has become attached to the analyte, the presence of the label can be detected using suitable detection systems, for example, optical detectors (for example, intensified CCD cameras), fluorescence detectors known in the art.

In one embodiment, the labels are enzymatic labels. In this case, a chromogenic, fluorogenic, or chemiluminescent enzyme substrate is contacted with the enzyme to produce a detectable product. It is understood in the art that chromogenic, fluorogenic, or chemiluminescent enzyme substrates are known or can be made for many different enzymes. Thus, any known chromogenic, fluorogenic, or chemiluminescent enzyme substrate capable of producing a detectable product in a reaction with a particular enzyme can be used in the present invention, including any of the chromogenic, fluorogenic, or chemiluminescent enzyme substrates disclosed in *The Handbook—A Guide to Fluorescent Probes and Labeling Technologies, Tenth Ed*, Chapter 10, http://probes.invitrogen.com/handbook/sections/1000.html, which is incorporated herein by reference in its entirety.

According to one embodiment in which the analyte is detected using a sandwich assay as described further herein in which the enzyme label is β-galactosidase, the enzyme substrate added to the array is a β-galactosidase substrate such as resorufin-β-D-galactopyranoside.

V. Assay Methods

The arrays of reaction vessels of the present invention can be used for several different assay methods. More specifically, the present invention provides for both (a) analyte detection and (b) quantification of analyte concentration in a sample.

Generally, the array of microwells of the present invention is exposed to an analyte of interest (or contacted with a sample containing an analyte of interest) and the analyte is captured by a capture component on the binding surface within each microwell under conditions suitable for capture of the analyte by at least one of the capture components, i.e. generally physiological conditions. For purposes of the present application, the term "immobilized" means captured, attached, bound, or affixed to a capture component on the binding surface. For example, in the context of using microwells, the interaction between any analyte molecule and the capture component on the binding surface of a microwell results in immobilization of the analyte molecule within that microwell.

According to one aspect of the invention, the sample of interest is placed in contact with the array of microwells of the present invention (or the array of the microwells is incubated in the sample) for a period of from about 30 minutes to about 12 hours depending upon the concentration of the analyte and the sample volume. In one embodiment, the array of microwells and sample are contacted for a period of from about 50 minutes to about 70 minutes. In a further embodiment, the incubation period is about 1 hour.

According to one embodiment, a wash step is performed after contacting the array of microwells with the sample. The wash step is intended to wash away any analytes or non-analyte molecules that are not bound to a capture component. Alternatively, no wash step is needed.

In one aspect of the invention, a secondary binding ligand then is added to the array of microwells. Generally, the secondary binding ligand is added if the method of detecting the analyte is an indirect assay such as a "sandwich assay" (when the analyte is not an enzyme), as described in further detail herein. The secondary binding ligand, as discussed above, will associate with or bind to the captured analyte and comprises detectable label, for example, an enzymatic component. The secondary binding ligand is added in an amount sufficient to ensure that a secondary binding ligand comes into contact with every bound analyte on the binding surface of the array of microwells. Alternatively, no secondary binding ligand is added, such as, for example, when the analyte is going to be detected directly.

When colored labels and spectroscopic labels are used, the labels can be detected using an appropriate detection system. In contrast, when the label is an enzymatic label, the enzymatic label is contacted with chromogenic fluorogenic, or chemiluminescent enzyme substrate to produce a detectable product.

In the case of enzymatic labels, a chromogenic, fluorogenic, or chemiluminescent enzymatic substrate as described above then is introduced or added to the array of microwells. The chromogenic, fluorogenic, or chemiluminescent enzymatic substrate is provided in an amount sufficient to contact any captured analyte that is either an enzyme itself or is coupled to an enzyme, for example, via an enzyme-labeled antibody. The chosen enzyme substrate reacts with or is modified by the enzymatic component such that the reaction produces a chromogenic, fluorogenic, or chemiluminescent product and thus an optical signal. The presence of the chromogenic, fluorogenic, or chemiluminescent product in the array of reaction vessels (as described below) can provide information about the identity and/or concentration of an analyte based on the interaction of the analyte with the capture component and the enzymatic substrate (and the secondary binding ligand, in some cases).

In one embodiment of the present invention, the array of microwells are sealed after the enzymatic substrate is added to form an array of reaction vessels. That is, a sealing component is placed in contact with the face of the array of microwells, thereby fluidly isolating each microwell and sealing its contents therein. A "sealing component," as used herein, is defined as any material or device large enough to cover the entire array of microwells and capable of contacting the exterior surface of the array of microwells (for example, the cladding of a fiber optic bundle) such that each reaction vessel thus formed is sealed or isolated such that the contents of each reaction vessel cannot escape the reaction vessel. According to one embodiment, the sealing component is a silicone elastomer gasket that is placed against the array of microwells with a uniform pressure across the entire substrate. By sealing the contents in each microwell, the enzymatic reaction can proceed within the reaction vessel thus formed, thereby producing a detectable amount of the chromogenic, fluorogenic, or chemiluminescerit product that is retained in the reaction vessel for detection purposes. That is, the enzyme converts the substrate into a chromogenic, fluorogenic, or chemiluminescent product that builds up to a locally high concentration in each sealed reaction vessel, generating a detectable chromogenic, fluorogenic, or chemiluminescent signal.

According to one embodiment, the present invention provides for a microscope system equipped with a mechanical platform that applies the sealing component. The platform is positioned beneath the microscope stage on the microscopy system. After the enzymatic substrate have been added to the array of microwells, the sealing component is sandwiched between a flat surface (such as, for example, a microscope slide) and the array of microwells using uniform pressure applied by the mechanical platform.

The assays for detecting analytes may be run under a variety of experimental conditions, as will be appreciated by those in the art. A variety of other reagents may be included in the screening assays. These include reagents like salts, neutral proteins, e.g. albumin, detergents, etc, which may be used to facilitate optimal protein-protein binding and/or reduce non-specific or background interactions. Also, reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

The reaction vessels exhibiting enzymatic activity or changes in their optical signature may be identified by a conventional optical train and optical detection system. Depending on the particular enzymatic substrates used and the operative wavelengths of their products, optical filters designed for a particular wavelengths may be employed for optical interrogation of the reaction vessels. In a preferred embodiment, the array of reaction vessels of the present invention are formed directly as part of a fiber optic bundle.

According to one embodiment, the array of reaction vessels of the present invention can be used in conjunction with an optical detection system such as the system described in U.S. application Ser. No. 09/816,651, which is incorporated herein by reference in its entirety. For example, according to one embodiment, the array of reaction vessels of the present invention is the distal end of a fiber optic assembly comprising a fiber optic bundle constructed of clad fibers so that light does not mix between fibers. As depicted in the Ser. No. 09/816,651, the proximal end of the bundle is received by a z-translation stage and x-y micropositioner.

The optical detection system of U.S. application Ser. No. 09/816,651 operates as follows. Light returning from the distal end of the fiber optic bundle is passed by the attachment to a magnification changer which enables adjustment of the image size of the fiber's proximal or distal end. Light passing through the magnification changer is then shuttered and filtered by a second wheel. The light then is imaged on a charge coupled device (CCD) camera. A computer executes imaging processing software to process the information from the CCD camera and also possibly control the first and second shutter and filter wheels.

The array of reaction vessels of the present invention may be integral or attached to the distal end of the fiber optic bundle using a variety of compatible processes. Microwells are formed at the center of each individual fiber of the fiber optic bundle and reaction vessels are formed by sealing this array of microwells with a sealing component. Thus, each optical fiber of the fiber optic bundle conveys light from the single microwell formed at the center of the fiber's distal end. This feature is necessary to enable the interrogation of the optical signature of individual reaction vessels to identify reactions in each microwell. Consequently, by imaging the end of the bundle onto the CCD array, the optical signatures of the reaction vessels are individually interrogatable.

A. Detection

As discussed previously, the detection system will depend upon the label being detected. For example, when the label is an optical label, spectroscopic label or radiolabel, the presence of the label can be determined using commercially available detectors known in the art.

When the label is an enzymatic label, the label can be detected directly (for example, when the analyte has inherent enzyme activity) or indirectly (for example, when the analyte does not exhibit enzyme activity) via techniques known in the art. In other words, if the analyte is an enzyme, the analyte can be identified by a direct method of detection. Alternatively, if the target analyte is not an enzyme and thus cannot produce a chromogenic, fluorogenic, or chemiluminescent product in the presence of an enzymatic substrate, the analyte is identified by an indirect method of detection.

The direct method of detection, which involves a analyte that is an enzyme, proceeds as follows. First, the sample of interest and the array of microwells are placed in contact as described in further detail above under suitable conditions. The enzymatic substrate is added either simultaneously with the sample or after addition of the sample.

After sealing the microwells, the presence or absence of the analyte in any given reaction vessel then is detected by optical interrogation. That is, any change in the optical signal caused by production of a chromogenic, fluorogenic, or chemiluminescent product is detected. In any reaction vessel containing the analyte, the analyte modifies or acts upon the enzymatic substrate in some way, thereby resulting in the release of a chromogenic, fluorogenic, or chemiluminescent product, resulting in a change in the optical signal from the reaction vessel. The chromogenic, fluorogenic, or chemiluminescent product is then optically detected.

In one embodiment of the present invention, the array of microwells are sealed with the sealing component to form reaction vessels after the enzymatic substrate is added, as described above.

The indirect methods of detection involve an analyte that does not have enzymatic properties. Two indirect methods that can be used with the present invention are the "sandwich" assay and the "competitive" assay. It is contemplated that similar assay formats can be employed when the labels are optical labels, spectroscopic labels and radiolabels.

Figure 2A:
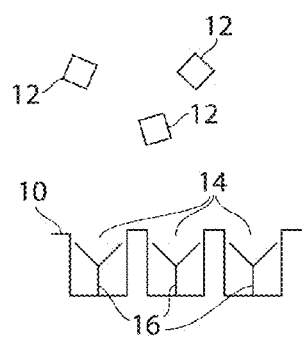
FIG. 2a, FIG. 2b, and FIG. 2c are side view cross-section schematics representing a sandwich assay, according to one embodiment of the present invention.
Figure 2B:
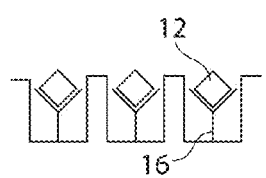

A sandwich assay can be performed as depicted in FIG. 2. First, the sample of interest and the array of microwells 10 are placed in contact as shown in FIG. 2a and as described in further detail above. Under suitable conditions, analyte 12 present in the sample is captured by the capture components 16 presented on the binding surfaces of the microwells 14, as shown in FIG. 2b. According to one embodiment, a wash step then is performed.

Figure 2C:
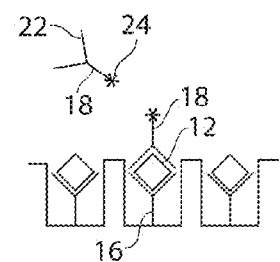

Next, a "secondary binding ligand" 18 is added to the array of microwells 10, as shown in FIG. 2c. Secondary binding ligands 18 are similar to capture components 16 in that they bind to the analyte 12. The secondary binding ligand 18 may be the same or different from the capture component 16. The binding of the secondary binding ligand 18 to a captured analyte 12 forms a "sandwich" of sorts. In the absence of the analyte, the secondary binding ligand 18 is washed away.

A secondary binding ligand 18 has two components, a binding component 22 and an enzymatic label or a label that can capture an enzyme 24. The binding component 22 is the portion of the secondary binding ligand 18 that binds to the analyte 12. Typically, the secondary binding ligand 18 binds to a different portion of the analyte 12 than the capture component 16, because if both the capture component 16 and secondary binding ligand 18 were to bind to the same portion, the secondary binding ligand 18 would not be capable of binding to a captured analyte 12. Thus, the chosen secondary binding ligand 18 can bind to the analyte 12 while the analyte 12 is bound to the binding surface 14 via a capture component 16.

The label 24 is the portion of the secondary binding ligand 18 that exhibits enzymatic activity or can be used to subsequently to capture an enzyme. According to one embodiment, the label 24 is an enzyme attached to the secondary binding ligand 18.

Subsequently, the enzymatic substrate is added. In one embodiment of the present invention, the array of microwells are sealed after the enzymatic substrate is added to form reaction vessels, as described above. The presence or absence of the analyte in any given reaction vessel then is detected by optical interrogation. That is, any change in the optical signal caused by production of a chromogenic, fluorogenic, or chemiluminescent product is detected. In any reaction vessel containing the analyte and the secondary binding ligand, the enzyme associated with the secondary binding ligand modifies or acts upon the enzymatic substrate in some way, thereby producing a chromogenic, fluorogenic, or chemiluminescent product, resulting in a change in the optical signal from the reaction vessel. The product then is optically detected.

The competitive assay operates as follows. First, a labelled molecule is added to the array of microwells of the present invention, wherein the label is a enzyme or enzymatic component. In this embodiment, the chosen labelled molecule binds with the capture component such that the addition of the labelled molecule to the array results in labelled molecules being bound to capture components on the binding surface of the microwells.

Next, the sample of interest and the array of microwells are placed in contact as described in further detail above. The presence of the analyte in the array of microwells causes the displacement of the labelled molecule and binding of the analyte to the capture components. The displacement occurs for the following reason: in this embodiment, the chosen capture component is capable of binding to either of the labeled molecule or the analyte, thus resulting in a competitive binding situation. As a result, if a labelled molecule is bound to a capture component on the binding surface of a microwell and an analyte is added, the analyte will displace the labeled molecule under suitable conditions.

According to one embodiment, a wash step is then performed to remove any non-bound labeled molecules from the binding surface of the array of microwells.

Subsequently, the enzymatic substrate is added. As discussed above, according to one aspect of the invention, the array of microwells are sealed after the enzymatic substrate is added to form reaction vessels. Alternatively, the array of microwells are not sealed. The presence or absence of the analyte in any given reaction vessel then is detected by optical interrogation. But unlike the optical interrogations that are described above, in this interrogation it is the lack of a chromogenic, fluorogenic, or chemiluminescent product that indicates the presence of the analyte in the reaction vessel. In any reaction vessel containing the analyte, no enzymatic action occurs and no change occurs in the optical signal from the reaction vessel. In contrast, in any reaction vessel in which the labelled molecule is still present, an optical signal is detected.

In an alternative version of the competitive assay embodiment, both the labelled molecule and sample of interest are added to the array of microwells at the same time in fixed volumes. In this version, the analyte and labelled molecule compete directly for the binding sites on the capture components.

In addition, it is understood that the methods and compositions described herein can be used in a variety of multiplexed assays to detect the presence of one or more analytes in a sample. Exemplary multiplex assays are described in the following sections.

1. Multiple Different Capture Components to Same Target Analyte

The reaction vessel array of the present invention according to one embodiment utilizes a plurality of capture components that are directed to a single target analyte but are not identical. In other words, the binding components bind to different binding sites on an analyte. This embodiment thus provides for more than one different capture component on each binding surface or different capture components on different binding surfaces. In one example, a single analyte is interrogated by two or more capture components, each of which is capable of binding to different sites on the analyte. This adds a level of confidence to the assay as non-specific binding interactions can be statistically minimized. In this embodiment, when proteinaceous analytes are evaluated, preferred embodiments utilize capture components that bind to different parts of the target. For example, when two or more antibodies (or antibody fragments) to different portions of the same analyte protein are used as capture components, preferred embodiments utilize antibodies to different epitopes. Similarly, when nucleic acid analytes are to be evaluated, the redundant nucleic acid probes may be overlapping, adjacent, or spatially separated. However, it is preferred that two probes do not compete for a single binding site, so adjacent or separated probes are preferred.

In this embodiment, a plurality of different capture components may be used, with from about 2 to about 20 being preferred, and from about 2 to about 10 being more preferred, and from 2 to about 5 being particularly preferred, including 2, 3, 4, or 5. However, as above, more may also be used, depending on the application.

2. Multiple Different Capture Components To Multiple Target Analytes

In another embodiment, the reaction vessel array of the present invention uses a plurality of different capture components that are directed to a plurality of target analytes, which can be the same or different. This embodiment includes more than one different capture component on each binding surface or different capture components on different binding surfaces. In one example, two or more analytes may be provided to which two or more capture components on the same binding surfaces or on different binding surfaces are capable of binding.

In this embodiment, more than one target analyte can be identified. For example, two or more target analytes can be identified so long as, in the case of direct assays, each different analyte is a different enzyme or, in the case of indirect assays, each target is coupled to binding moieties conjugated with different labels. In one embodiment, the analytes are identified using multiple enzymatic substrates wherein each substrate produces a different color upon interaction with the appropriate enzyme. Thus, each target analyte can be distinguished based on the color produced by reaction with the enzymatic substrate. When labels other than enzymes are used, the different labels should have different characteristics so that each different label can be identified with the appropriate detector.

In an alternative approach, referred to as a sequential approach, the analytes are identified using the same or different labels. In this approach, the one or more analytes of interest are captured on one or more binding surfaces. Then a first labeled binding moiety that binds the analyte is permitted to bind to a first immobilized analyte. The presence of the label can be detected with an appropriate detection system. Thereafter, the first labeled binding moiety is removed, for example, by washing. Then a second labeled binding moiety that binds to a second, different analyte is permitted to bind to the second analyte. The presence of the label can be detected with an appropriate detection system. Thereafter, the second labeled binding moiety can be removed by washing and the process repeated as desired. It is understood that, in this approach, the same or different labels can be present in the first and second labeled binding moieties. It is understood that all the labels described herein can be used in this approach. When the label is a enzyme, it is understood that the sequential reactions can be performed using substrates, each of which produce the same or different colors.

In this embodiment, a plurality of different capture components can be used, with from about 2 to about 100 being preferred, and from about 2 to about 20 being especially preferred, and from 2 to about 10 being particularly preferred, including 2, 3, 4 or 5, 6, 7, 8, 9. However, as above, more may also be used, depending on the application.

In an another approach, referred to as a spatial approach, it is possible to use either (i) two different capture components disposed within separate regions of a binding surface, (ii) two different labeled binding moieties that are applied to an separate regions of a binding surface, or (iii) a combination or (i) and (ii).

In the first example of the spatial approach, different capture components are applied to different regions of the binding surface. For example, this can be achieved by placing micro-droplets on different regions of a fiber microwell array if it is used as a binding surface or to the sealing component if it is used as the binding surface. Each micro-droplet would contain a different capture component that would functionalize the surface it contacts with the different capture component. In this way, depending on the size of the droplets, it is possible to make a array of different capture components on the binding surface that are spatially discrete. The number of multiplexed analytes that could be detected in this manner would depend on the size of the different capture component regions and the size of the array of reaction vessels.

In the second example of the spatial approach, it is understood that the analytes of interest can be captured uniformly across a binding surface or within discrete regions of the binding surface. In this approach, however a first labeled binding moiety is applied to a first region of the binding surface and the presence of a first analyte is detected. Simultaneously or sequentially, a second labeled binding moiety is applied to a second region of the binding surface and the presence of a second analyte is detected.

It is understood that that each of the different assay configurations above, including the capture components directed to different analytes and the plurality of capture components directed to the same analyte, can also be utilized for quantification as described below.

In addition, under certain circumstances it is understood that the array of microwells may be reused during a subsequent assay. In this approach, a log of the wells that contained analyte in a first assay is recorded and then in a subsequent assay the wells that previously contained analyte are mathematically subtracted from the array of microwells used in the subsequent assay.

B. Quantification

According to one embodiment of the present invention, the methods, systems, and devices of the invention can be used to both detect the presence and concentration of an analyte in the sample. That is, there is a correlation between the percentage of reaction vessels containing one or more analyte molecules and the concentration of the analyte in the sample. Thus, the quantification method of the present invention allows for calculation of the amount of a analyte in a sample based on the percentage of reaction vessels that contain an analyte molecule.

The present invention is distinguished by its ability to quantify low numbers of individual molecules and is, therefore, well suited to measuring very low concentrations of target analyte. This ability is achieved by spatially isolating single analyte molecules, for example, in an array of reaction vessels, and then optionally generating and confining a chromogenic product, for example, a fluorescent label, in the reaction vessels. The presence of an analyte molecule can easily be counted in a binary fashion (zero when a molecule is absent; one when a molecule is present) due to the high concentration of chromogenic product in any reaction vessel that contains at least one analyte molecule.

Without being limited by theory, the quantification method is driven in part by the fact that the number and volume of reaction vessels employed govern the dynamic range of concentrations that can be determined by this technique. That is, based on the number and volume of the reaction vessels in an array of the present invention, an estimate can be made of the range of concentrations of target analyte in solution that allow for the concentration to be determined using the method of the present invention.

For example, for an array as disclosed in Example 2 with reaction vessels each having a volume of 46 fL, a solution having a concentration of $3.6 \times 10^{-11}$ Mβ-galactosidase will yield, on average, one enzyme molecule per vessel. However, it is important to note that distributing a solution having a target analyte concentration within the appropriate range into an array of reaction vessels will not result in the distribution of exactly one enzyme molecule per vessel; statistically, some vessels will have multiple molecules while others will have zero. In the case where the number of vessels containing one or more enzyme molecules to the number of vessels containing no enzyme molecule is high, the data can be fit to a Gaussian distribution. As the ratio of reaction vessels containing an enzyme molecule to the number of vessels containing no enzyme molecule approaches zero, the Poisson distribution applies. This limiting distribution is used to calculate the probability of rare events occurring in a large number of trials. For example, based on Poisson statistics, for a concentration of $3.6 \times 10^{-11}$ M, a distribution between zero and five enzyme molecules per container is predicted, with the most probable values being zero and one.

Equation 1 can be used to determine the probability of observing ν events based on the expected average number of events per trial, μ

$$P_\mu(\nu) = e^{-\mu}(\mu^\nu/\nu!)$$ Equation 1:

If the concentrations used are much less than $3.6 \times 10^{-11}$ M, the expected average becomes exceptionally low, the distribution is narrowed, and the probability of observing anything other than 0 or 1 events per trial is improbable in all experimental cases. At these low concentrations, the relationship between the percentage of active reaction vessels and the bulk enzyme concentration is approximately linear. Thus, based on this knowledge, the array of the present invention can be used to determine the concentration of a target analyte in a sample by a simple digital readout system, i.e., "counting" of active wells, as described herein.

According to one embodiment, the quantification method of the present invention can be performed as follows. The method is a digital readout system (also referred to as a "binary readout system") that includes first detecting the analytes in the array of reaction vessels by any detection method described above. The number of reaction vessels is then counted and a percentage of the total number of reaction vessels is calculated. That is, utilization of a yes or no response, in conjunction with the high-density array of reaction vessels, permits the digital readout of bulk concentrations of analyte molecules labeled with a label of interest, for example, the enzyme, β-galactosidase. This readout is accomplished by counting the vessels containing an active enzyme molecule across the array, with the resulting "active well" percentage correlating to the concentration of analyte assuming one enzyme label per target molecule. Given the large number of vessels simultaneously interrogated in the array of the present invention, the ratio of enzyme molecules to reaction vessels could be 1:1000 or less, as the large number of wells provides a statistically significant signal even at this low ratio.

Without being limited by theory, it is believed that the quantification method of the present invention is only limited by the number of individual reaction vessels that can be fabricated and interrogated. Thus, expanding the number of reaction vessels will increase both the dynamic range and the sensitivity of the assay.

The limitations of this technique are realized above and below the thresholds of the dynamic range. As the concentration goes below the lower limit of the dynamic range, the number of enzyme molecules is too low to observe sufficient occupied wells and, therefore, the number of wells must be increased in order to make sure that a statistically significant number of them are occupied by enzyme molecules. Results for extremely dilute concentrations have large relative errors associated with them, due to the very small number of reaction vessels that are expected to show activity. Slight deviation from the expected Poisson value, in this case, will result in a large error. The ultimate upper limit to this technique occurs when 100% of the reaction vessels contain at least one enzyme molecule. At this limit, discrimination between two solutions of high enzyme concentrations is not feasible.

In the range where the fraction of reaction vessels containing at least one molecule is less than about 20%, the probability that any well contains two or more analyte molecules is very small and the number of analyte molecules closely matches the number of occupied reaction vessels. Between 20% occupied and 100% occupied, an increasing number of wells will contain more than one molecule, however Gaussian statistics can still be used to correlate occupancy fraction with concentration until the occupancy fraction reaches 100%.

In practice, non-specific signal creates a lower "noise floor" and faulty reaction vessels create an upper "noise ceiling." Furthermore, with reference to the number of wells occupied or not occupied by analyte, statistically significant occupancy can be determined using standard statistical methods known in the art. For example, a statistically significant measurement can be one that is three times the standard deviation from the mean.

If desired, the practical dynamic range of the method can be increased in several ways. In one approach, the sample is diluted by a factor of 10 or more. Both the sample and the diluted sample can be assayed concurrently using the method of this invention. The dynamic ranges of the two assays will overlap, but be offset by the dilution factor, hence extending the dynamic range.

In a second approach, the amount of signal in each reaction vessel is measured at multiple time points prior to the time when all of the reaction vessels are positive for analyte. The fraction of wells that are positive at an early timepoint can be calibrated against a known reference standard to determine the concentration of the sample being analyzed. In the embodiment of the invention that utilizes a fiber optic bundle and a CCD camera, it is straightforward to image all of the wells in near real-time.

In a third approach, multiple arrays of reaction vessels can be used with differing volumes, differing areas of binding surface, or differing density of concentration of capture components on the binding surface. These arrays can be constructed as either distinct arrays or as one large array with sub-arrays with varying characteristics. Since the probability of an analyte molecule being detected in a given reaction vessel is related to volume, binding surface, and capture component density, the sub-arrays may be designed to cover different sensitivity ranges. If those ranges overlap, the effective range of the combined array can be extended.

In another aspect, the invention provides a method of determining the concentration of an analyte in a fluid sample to be tested. The method comprises the steps of (a) dividing the fluid sample into an array of wells, so that, for substantially all of the wells, each well contains either no analyte or a single molecule of the analyte; (b) determining the presence or absence of the analyte in each well to provide a number of wells in the array that contain the analyte; and (c) determining the concentration of the analyte in the fluid sample to be tested from the number of wells in the array that contain the analyte.

In one embodiment, less than about 20% of the total number of wells contain at least one molecule. Under these circumstances, the number of wells containing at least one molecule falls within the linear range of a Poisson distribution. In another embodiment, less than about 20% of the total number of wells contain about one molecule. In another embodiment, more than about 20% but less than about 60% of the total number of wells contain at least one molecule. Under these circumstances, the number of wells containing at least one molecule falls within the non-linear range of a Poisson distribution. In another embodiment, more than about 20% but less than about 60% of the total number of wells contain about one molecule. In another embodiment, more than about 60% but less than about 95% of the total number of wells contain at least one molecule. Under these circumstances, the number of wells containing at least one molecule falls within the highly non-linear range of a Poisson distribution. In another embodiment, more than about 60% but less than about 95% of the total number of wells contain about one molecule.

In another aspect, the invention provides a method of determining the concentration of an analyte in a fluid sample to be tested. The method comprises the steps of: (a) dividing the sample to be tested into a plurality of second, smaller fluid samples of equal volume so that a statistically significant fraction of the second, smaller fluid samples contain either no analyte or a single molecule of the analyte; (b) determining the presence or absence of the analyte in each of the second, smaller fluid samples so as to identify the number of second, smaller fluid samples that contain the analyte; and (c) determining the concentration of the analyte in the sample to be tested from the number of second, smaller samples that contain the analyte.

In this approach, the statistically significant fraction of the second, smaller fluid samples that contain either no analyte or a single molecule of the analyte is defined as 50%, optionally 75%, optionally 95% of the total number of second fluid samples that contain either no analyte or a single molecule of analyte.

In one aspect of the present invention, the array can also be used to analyze enzyme kinetics. "Enzyme kinetics" as used herein refers to the study of the rates of enzyme-controlled reactions. It is understood in the art of enzyme kinetics that the rate of an enzymatic reaction at low substrate concentrations is proportional to the substrate concentration (is "substrate dependent"). This is referred to as first order. It is further understood that the rate of the reaction at high substrate concentrations reaches a maximum rate and is independent of substrate concentration because the reaction becomes saturated. Thus, if reaction velocity is plotted as a function of substrate concentration, the line initially increases linearly with an increase in substrate and then begins to level off as substrate concentration approaches saturation.

Thus, according to one embodiment, the kinetics of any particular enzyme can be studied using the present system and array. Reaction velocity varies across enzymes for various reasons, including, for example, reaction inhibition caused by allosteric inhibition. The array of the present invention allows for study of these varied kinetic characteristics.

According to one embodiment, kinetics are examined in the following fashion. The target analyte is allowed to bind to the capture component, the substrate is added, and the reaction vessel is sealed. Given that a finite amount of substrate is present in the reaction vessel and that no further substrate can be added due to the sealing of the vessel, the reaction velocity can be determined based on the amount of chromogenic product detected over time.

VI. Exemplary Uses of the Present Invention

The system and array of the present invention has many uses. For example, the array has application to fundamental enzymology studies, as well as digital concentration measurements. Further, the array permits studies with multiple different enzymes and extends the limits of ultra-low detection for protein and DNA targets. With the ability to simultaneously monitor a large array of reaction vessels, single molecule enzymology can be used to resolve individual enzyme molecule behavior from bulk kinetic signal.

Another use, for example, is environmental monitoring of bacteria or viruses or both. An environmental sample potentially containing certain bacteria can be placed in contact with an array of the present invention. To detect the bacteria, the bacteria cells are lysed and a bacterial enzyme (or more than one enzyme) is targeted for detection. According to one embodiment, the cells are lysed prior to being added to the array. Alternatively, the cells are captured and a lysing step occurs on the array prior to detection. In a further alternative, no lysis may be necessary if a cell surface marker is targeted. For example, the bacteria or virus of interest can be captured with an antibody that is specific to a surface marker on the target, and then the capture can be detected with a sandwich-type assay by adding an enzyme-labelled antibody that binds to the target in another location.

Another use, for example, involves measuring gene expression. In one embodiment, the target analytes are cells and these are introduced into the reaction vessels of the array under conditions such that some reaction vessels contain single cells. This is the first step in measuring gene expression, which can be done if desired at the whole cell level by detecting surface proteins and secreted proteins. Alternatively, the cells can be lysed and transcripts (or other components) from the cells can be interrogated. In one embodiment, each site contains one or no transcripts. In one embodiment, normal and cancer cells are compared. The cell to cell variation in gene expression can be addressed by examining gene expression at the single cell level.

Although the present invention has been described herein with reference to preferred embodiments, persons skilled in the art will recognize that changes may be made in form and detail without departing from the spirit and scope of the invention.

EXAMPLES

Example 1

In this example, a proof-of-concept binding assay is performed using enzymatic signal amplification in an array of femtoliter sized reaction vessels. More specifically, various assays are performed to detect varying amounts of streptavidin-β-galactosidase (SβG) in solution using a biotinylated array of the present invention and then the correlation between the number of wells with captured SβG molecules and the concentration of the SβG in the sample is examined.

In this example, an etched fiber optic array is used to create a collection of femtoliter sized reaction vessels, each specifically functionalized and capable of capturing enzyme-labeled target molecules. Single enzyme molecules are confined to individual reaction vessels and catalyze the production of a sufficient number of fluorescent product molecules to generate a positive signal. At low target molecule concentrations, only a percentage of the capture sites bind a target molecule, enabling a binary readout of target concentration from the high-density array.

Materials

The reactor vessel arrays in this example are generated using an acid etch of the distal face of a polished 1 mm fiber optic array, consisting of 24,000 individual 4.5 μm optical fibers. The core fiber material is silica, and the cladding around each fiber is germania-doped silica, which etches at a slower rate. The 4.5 μm fibers are etched to a depth of 2.9 μm, creating an array of reactor vessels, each with a 46 fL volume (see FIG. 1a).

The fibers were first modified with an aminopropyl silane bound to both the core and cladding surfaces (see FIG. 1b). To avoid biotin attachment to the cladding, the amino-silanized fibers were polished for 10 seconds with 0.3 μm lapping film, which removed the top amino-silanized cladding layer from the fiber array (see FIG. 1c). After polishing, NHS-biotin was attached to the amino groups on the well surfaces (see FIG. 1d).

Methods

Figure 3A:
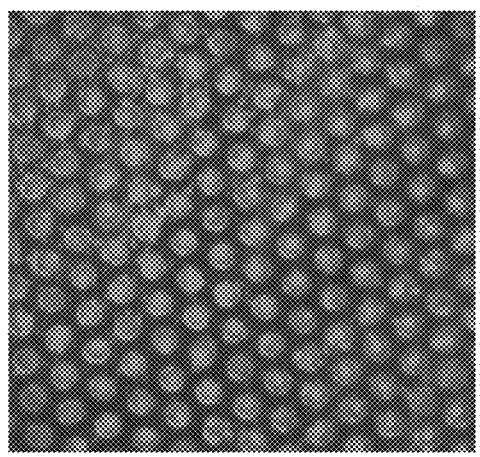
FIG. 3a and FIG. 3b are photographs depicting Streptavidin Alexa Fluor 568° binding to (a) an unpolished biotin-modified array of microwells at the distal end of a fiber optic bundle; and (b) a polished biotinmodified array of microwells, according to one embodiment of the present invention.
Figure 3B:
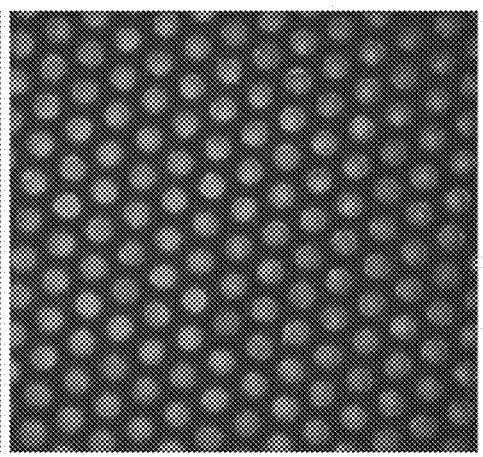

First, the effectiveness of the capture component was tested. To test the effectiveness of the biotinylation of the substrate, streptavidin Alexa Fluor 568® was attached directly to the biotin groups on the surfaces of both a polished and an unpolished fiber, followed by image acquisition of the modified surface (see FIG. 3). FIG. 3 shows Streptavidin Alexa Fluor 568® binding to (a) an unpolished biotin modified fiber optic array, and (b) a polished biotin modified fiber optic array. As seen in image (a), streptavidin binding occurred on all surfaces, in comparison to image (b), where binding occurred only on the surfaces of the microwell reactors. Thus, the unpolished fiber shows dye over the entire array including the cladding surface, while the polished fiber shows dye localized only on the well surfaces.

Subsequent to array modification, the biotinylated fiber arrays were incubated for 1 hour at room temperature in 150 μL PBS buffer containing varying amounts of SβG. The concentration of the SβG was chosen so that during the incubation time, statistically either one molecule or no molecules would bind to each well. The arrays were then washed repeatedly in PBS buffer, to ensure that unbound target was removed.

For a binary readout of SβG binding, the fiber array was loaded and secured on an upright microscope system equipped with a mechanical platform. A solution of β-galactosidase substrate, resorufin-β-D-galactopyranoside (RDG), was introduced to the distal end of the fiber containing the reaction vessels, and subsequently sealed. The substrate was sealed using a 0.01-inch thick silicone elastomer gasket sandwiched between a microscope slide and the fiber array by means of a mechanical platform located beneath the microscope stage. This platform applied a uniform pressure to the gasket material, across the entire bundle, sealing off each reaction chamber and enabling well to well interrogation of enzyme activity. β-galactosidase hydrolyzes RDG to form resorufin, which builds up to a locally high concentration in each sealed reaction vessel, generating a detectable fluorescent signal (FIG. 4).

FIG. 4 depicts a portion of the fiber array for each experiment. Each of the experiments tested a different sample having a different concentration of SβG. The concentrations for each experiment were as follows: (a) 128 amol, (b) 51 amol, (c) 25 amol, (d) 7.5 amol, and (e) 2.6 amol. FIG. 4(f) depicts the control.

Analysis of over 5000 reaction vessels for each experiment allowed for a correlation between the percentage of reaction vessels that captured an enzyme molecule and the amount of enzyme present in the interrogated sample. The variation seen in the intensity differences from active well to active well is most likely a result of molecule-to-molecule variation in catalytic activity, in combination with surface effects, which may modulate the relative activities of enzyme molecules based on their orientation to the reaction chamber surface.

Two control experiments were also conducted to ensure that the binding of enzyme to the surface of the reactors was based exclusively on the biotin-streptavidin interaction, and not on non-specific binding to the glass surface. One control experiment consisted of an etched, unmodified fiber incubated with the most concentrated SβG target solution (128 amol in 150 μL). The second control experiment was performed using the modified fiber incubated in a solution of β-galactosidase lacking streptavidin (128 amol in 150 μL). Both control experiments generated a negligible active well percentage (less than 0.06%, versus 0.2% for the 2.6 amol experiment discussed below).

Results

Figure 5:
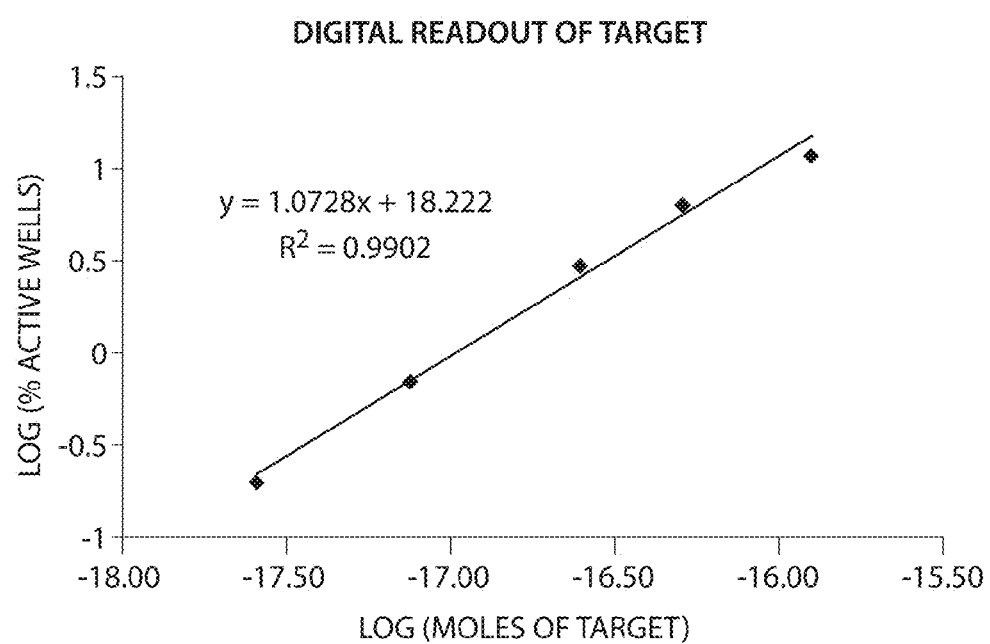
FIG. 5 is a chart depicting a log-log plot of the moles of analyte present in a sample with the resulting percentage of active reaction vessels, according to one embodiment of the present invention.

FIG. 5 depicts a log-log plot of the moles of target present in a sample with the resulting percentage of active reaction vessels. The linear relationship between the percentage of active reaction vessels and the moles of target in the log-log plot shown in FIG. 5 suggests that a binary readout detection method can be used for the detection of real targets such as DNA and antigens. This method permits rapid analysis and accurate concentration information via digital readout, while maintaining a straightforward assay procedure.

It is also interesting to note that the lowest limit of detection (LOD) for binding streptavidin-β-galactosidase (SβG) to a biotinylated femtoliter array in this example was 2.6 amoles (150 μL of 17 fM solution) using a target incubation time of 1 hour.

Example 2

In this example, single molecules of β-galactosidase were monitored using a 1 mm diameter fiber optic bundle with over $2.0 \times 10^5$ individually sealed, femtoliter microwell reactors. By observing the buildup of fluorescent products from single enzyme molecule catalysis over the array of reaction vessels and by applying a Poisson statistical analysis, a digital concentration readout was obtained.

Materials 1 mm bundled 4.5 µm optical fibers were purchased from Illumina (San Diego, Calif.). β-galactosidase and Ru(bpy)$_3$Cl$_2$ was obtained from Sigma-Aldrich (St. Louis, Mo.). Resorufin-D-β-galactopyranoside was purchased from Molecular Probes (Eugene, Oreg.). 0.01-inch non-reinforced gloss silicone sheeting material was purchased from Specialty Manufacturing Inc. (Saginaw, Mich.). All other chemicals used were of reagent grade and obtained from Sigma-Aldrich (St. Louis, Mo.).

A custom-built, upright epifluorescence imaging system acquired all fluorescence images using a mercury light source, excitation and emission filter wheels, microscope objectives, and a CCD camera (QE, Sensicam). Filter wheels and shutters were computer controlled and analysis was performed with IPlab software (Scanalytics, Fairfax, Va.). The system was equipped with a fastening device to fix the fiber optic array onto the system through the entire experiment. A mechanical platform beneath the stage was used to house the silicone-sealing layer, which was subsequently brought into contact with the distal end of the fiber array, sealing off each reaction vessel. All measurements were performed with femtowell arrays at the distal end of the optical fiber bundle.

Figure 6A:
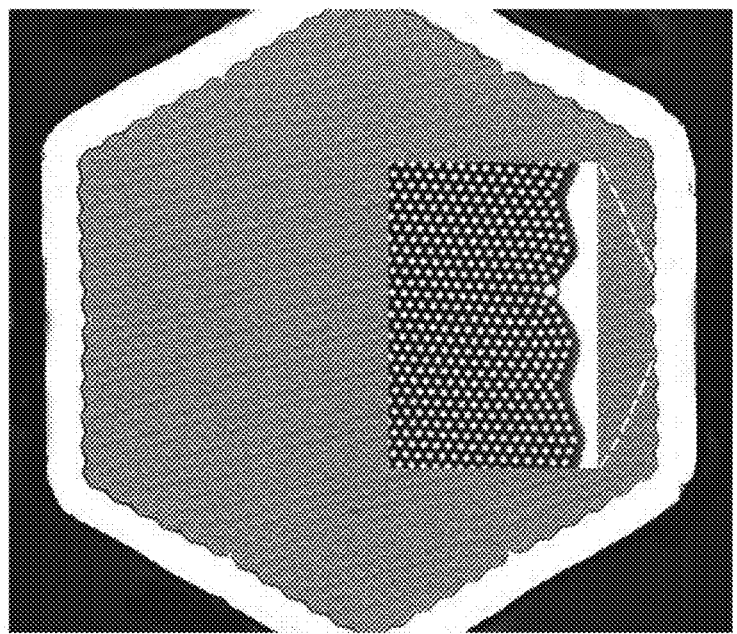
FIG. 6a is a microscopic photograph of an entire of micro wells formed at the distal end of a fiber optic bundle and an inset close-up of the array of microwells, according to one embodiment of the present invention.
Figure 6B:
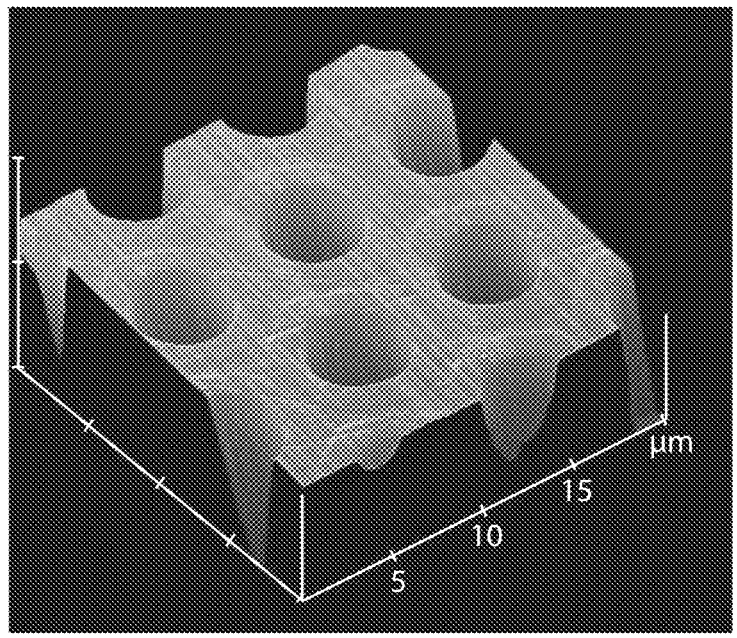
FIG. 6b is an AFM image of a portion of an etched array of microwells, according to one embodiment of the present invention.

Optical fiber bundles containing approximately 2.4×10$^5$ individual 4.5 µm diameter optical fibers were used as the substrate for fabricating femtoliter reaction vessel arrays. The well volume can be precisely controlled, as etch depth varies with etch time and etchant concentration. The optical fibers used in these experiments were etched to a depth of approximately 2.9 µm, yielding a 46 fL well volume. FIG. 6 depicts images of the etched surface of the fiber optic bundles. More specifically, FIG. 6a depicts the entire fiber array and close-up microscope images of the fiber bundle, emphasizing the regularity of both the array and each individual optical fiber. Further, FIG. 6b is an AFM image of a portion of the etched surface, showing wells created from the etching process.

Methods

Assay.

For the β-galactosidase assay, the substrate used was resorufin-β-D-galactopyranoside. After the individual wells in the array were sealed in the presence of enzyme and substrate, the fluorescence intensity was monitored across the array of vessels for the enzymatic product, resorufin (ex 558 nm/em 573 nm). A 100 µM solution of resorufin-D-β-galactopyranoside (RDG) was prepared in 100 mM Tris buffer pH 8.0 containing 2.0 mM KCl and 0.1 mM MgCl$_2$. All enzyme solutions were prepared from previously aliquoted and frozen stock samples in the same reaction buffer. Just prior to experimentation, the two samples were centrifuged for 2 min at 7000 RPM to remove any particulate material that could interfere with the mechanics of the silicone seal. Approximately 1 cm$^2$ of silicone and a microscope slide were cleaned with absolute ethanol. The silicone sheeting was placed on the surface of the glass, to which it adhered. Subsequently, 75 µL volumes of enzyme and RDG solutions were mixed on the silicone gasket using a pipette. The gasket was mechanically raised towards the distal end of the fiber bundle until it experienced resistance, suggesting that a seal was formed. An initial fluorescence image was acquired, followed by periodic image acquisition for approximately 2 hr.

Sealing Component.

To seal the femtoliter array, a 0.01-inch thick silicone elastomer gasket was sandwiched between a microscope slide and the fiber array using a mechanical platform. This platform applied uniform pressure to the gasket material, across the entire bundle, sealing off each microwell to create the reaction vessels.

Figure 7A:
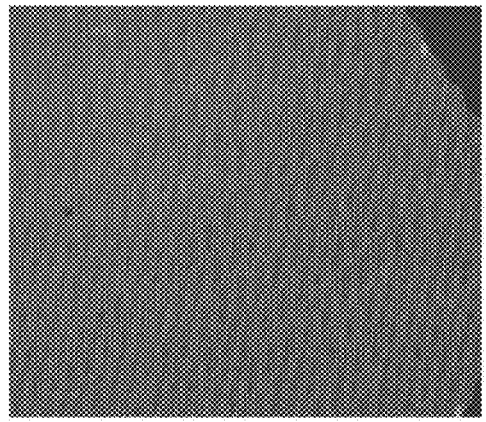
FIG. 7a, FIG. 7b, and FIG. 7c depict enclosure of the reaction vessels and evaluation of the sealing component, according to one embodiment.
Figure 7B:
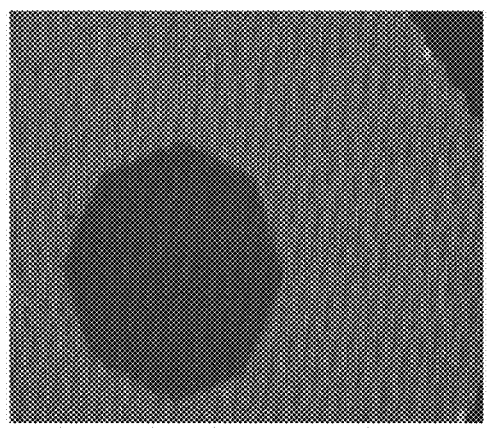
Figure 7C:
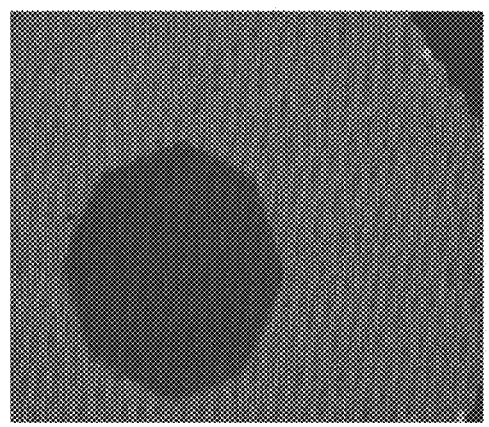

The silicone/glass seal used to create and isolate the femtoliter containers was inspected for its sealing ability by performing a photobleaching experiment (see FIG. 7). FIG. 7 depicts enclosure of a solution into the microchambers and evaluation of the silicone seal for integrity. FIG. 7a depicts a solution of Ru(bpy)$_3$Cl$_2$ enclosed into the array of chambers as observed by the red fluorescence across the array. FIG. 7b depicts a small octagonal portion of the fiber bundle that was photobleached via UV light. FIG. 7c depicts the array 60 minutes later. As shown in the figure, diffusion of Ru(bpy)$_3$Cl$_2$ from one well to another as a result of an imperfect silicone seal would display increased fluorescence intensity in photobleached wells and was not observed. This experiment substantiated the integrity of the seal for its ability to successfully isolate the array of vessels. Enzyme molecule denaturation on the glass surface was prevented by blocking with a BSA blocking buffer. Enzyme to vessel ratios used ranged from 1:5, down to 1:500, achieving accurate detection over two orders of magnitude.

Photobleaching Experiment.

A solution of 1 mM Ru(bpy)$_3$Cl$_2$ in DI water was used for the photobleaching experiments. A piece of silicone, approximately 1 cm$^2$, and a microscope slide were cleaned with absolute ethanol using lint-free swabs. The silicone sheeting was placed on the surface of the glass, to which it adhered. 50 µL of the Ru(bpy)$_3$Cl$_2$ solution was placed on the silicone, and subsequently brought into contact with the fiber bundle, to enclose the solution in the individual vessels. Using a field stop on the imaging system, UV light was used to illuminate a small portion of the array for 10 minutes, photobleaching the Ru(bpy)$_3$Cl$_2$. The field stop was then opened, and an image was acquired, displaying the difference in fluorescence. The array was then allowed to rest with the seal maintained. A final image was taken after 60 minutes, confirming the integrity of the seal.

As discussed above, the number and volume of reaction vessels employed govern the dynamic range of concentrations that can be determined by this technique. The reaction vessel volumes employed in this example were 46 fL (vide infra); therefore, it was calculated that a solution of 3.6×10$^{-11}$ M β-galactosidase will yield, on average, one enzyme molecule per vessel. As also discussed above, if the concentrations used are much less than 3.6×10$^{-11}$ M, the expected average becomes exceptionally low, the distribution is narrowed, and the probability of observing anything other than 0 or 1 events per trial is improbable in all experimental cases. At these low concentrations, the relationship between the percentage of active reaction vessels and the bulk enzyme concentration is approximately linear. After waiting for sufficient time to allow enzyme catalysis to occur, individual vessels were interrogated for an on/off response, correlating to each vessel either possessing or lacking enzymatic activity.

The substrate resorufin-D-β-galactopyranoside (RDG) was used as the substrate for experiments, which was sealed into all the vessels, along with the trapped enzyme molecules, using a silicone gasket material and mechanical arm. The expected percentages of active wells were calculated for each concentration used by applying the Poisson distribution statistics.

Results

Figure 8A:
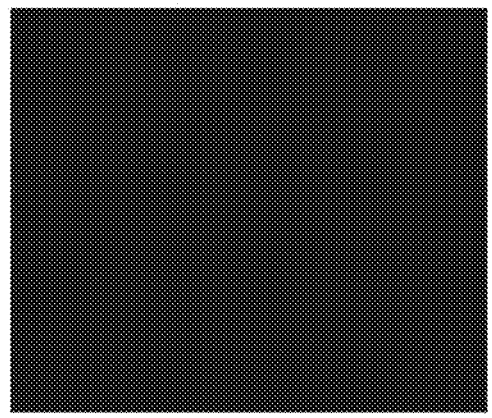
FIG. 8a, FIG. 8b, and FIG. 8c are microscopic photographs depicting detection of the activity of single molecules of β-galactosidase, according to various embodiments of the present invention.
Figure 8B:
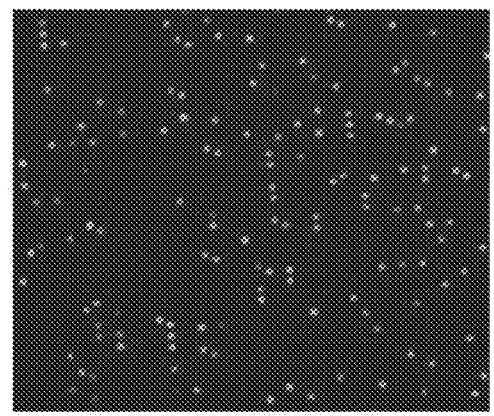
Figure 8C:
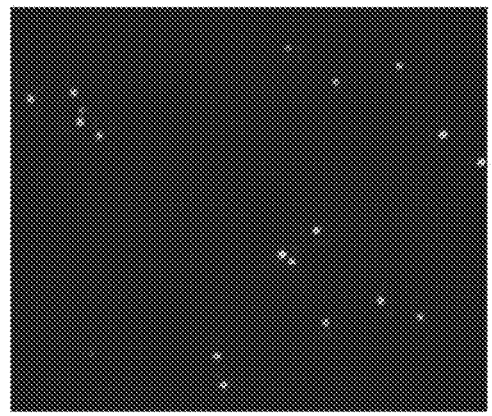

As shown in FIG. 8, for the β-galactosidase assay, different bulk solution enzyme concentrations correspond to different ratios of enzyme to vessel volume, resulting in variation in the percentage of vessels that contain an enzyme molecule. FIG. 8 depicts the detection of the activity of single molecules of β-galactosidase. FIG. 8a is a background image of a portion of the array, while FIG. 8b depicts an image taken of a portion of a 1:5 enzyme to vessel assay, and FIG. 8c shows a 1:80 enzyme to vessel assay.

Table 1 is a comparison of each experimental result with the percentage of occupied vessels calculated from the Poisson distribution. As shown by the data in the table, the array measurements successfully correlated with the number of single enzyme β-galactosidase molecules over the entire range of interrogated concentrations. There is minor disparity in the observed signals as a result of molecule-to-molecule variation in catalytic activity. This result is most likely due to the inherent stochastic nature of enzymes, in addition to surface effects, resulting in modulation of enzyme activity.

TABLE 1

Digital Readout of Enzyme Concentrations

| Enzyme to well ratio | Concentration (M) | Poisson % of active wells | Actual % active |
|---|---|---|---|
| 1:5 | 7.20E-12 | 18.2 | 14.9 |
| 1:10 | 3.60E-12 | 9.5 | 11.5 |
| 1:20 | 1.80E-12 | 4.9 | 5.6 |
| 1:40 | 9.00E-13 | 2.5 | 3.5 |
| 1:80 | 4.50E-13 | 1.2 | 1.5 |
| 1:100 | 3.60E-13 | 1.0 | 1.1 |
| 1:200 | 1.80E-13 | 0.5 | 0.3 |
| 1:500 | 7.20E-14 | 0.2 | 0.1 |

Table 1. Digital readout from the arrays. The actual percentage of chambers exhibiting activity, in comparison to the expected percentage calculated from the Poisson distribution, are listed for the various concentrations analyzed.

The variation between the calculated and experimental results can be attributed to the intrinsic variability associated with the probability distribution, as well as experimental error in the preparation of enzyme solutions.

Example 3

In this example, a proof-of-concept sandwich assay is performed to detect a non-enzymatic target protein using an array of femtoliter sized reaction vessels (see, FIG. 9). More specifically, various assays were performed to detect varying amounts of interferon-inducible protein 10 (IP-10) in solution using an array with the capture component, an anti-IP-10 antibody, disposed upon the surface of the reaction vessels. The captured target IP-10 then was labeled with a secondary binding ligand (biotin-labeled anti-IP-10) and strepatavidin-conjugated β-galactosidase (SβG). The correlation between the number of wells with captured SβG molecules and the concentration of IP-10 in the sample was examined.

Materials

The reactor vessel arrays in this example were generated using an acid etch of the distal face of a polished 1 mm fiber optic array, consisting of 24,000 individual 4.5 µm optical fibers. The core fiber material was silica, and the cladding around each fiber was germania-doped silica, which etches at a slower rate. The 4.5 µm fibers were etched to a depth of 2.9 µm, creating an array of reactor vessels, each with a 46 fL volume (see FIG. 1a).

The fibers were first modified with an aminopropyl silane (see FIG. 1b). These amine-presenting fibers then were reacted with 100 mM N,N'-disuccinimidyl carbonate (DSC) to activate them with an ester of succinimide. The resulting substrates then were reacted with 0.1 mg/mL of anti-IP-10 capture antibody and washed.

Methods

Subsequent to array modification, the fiber arrays having anti-IP-10 antibody disposed thereon were incubated for 1 hour at room temperature in 150 µL PBS buffer containing varying amounts of IP-10. The captured IP-10 arrays then were incubated with 2 µg/mL of a secondary binding ligand, i.e., the detection anti-IP-10 antibody labeled with biotin. These arrays then were incubated with 300 µM of SβG to label the bound IP-10 molecules with enzyme. The arrays then were washed repeatedly after each incubation in PBS buffer, to ensure that unbound target, antibody and SβG was removed.

For a binary readout of SβG bound to IP-10, the fiber array was loaded and secured on an upright microscope system equipped with a mechanical platform. A solution of β-galactosidase substrate, resorufin-β-D-galactopyranoside (RDG), was introduced to the distal end of the fiber containing the reaction vessels, and subsequently sealed. The substrate was sealed using a 0.01-inch thick silicone elastomer gasket sandwiched between a microscope slide and the fiber array by means of a mechanical platform located beneath the microscope stage. This platform applied a uniform pressure to the gasket material, across the entire bundle, sealing off each reaction chamber and enabling well to well interrogation of enzyme activity. β-galactosidase hydrolyzes RDG to form resorufin, which builds up to a locally high concentration in each sealed reaction vessel, generating a detectable fluorescent signal.

Analysis of over 5000 reaction vessels for each experiment allowed for a correlation between the percentage of reaction vessels that captured an enzyme molecule and the amount of IP-10 present in the interrogated sample.

Results

Figure 10:
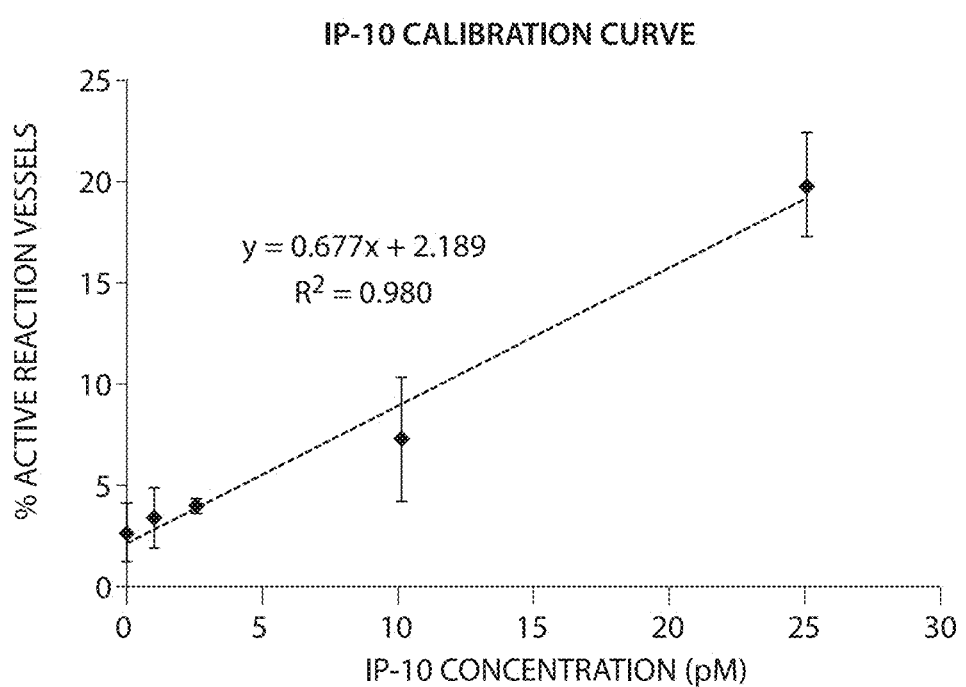
FIG. 10 depicts a plot of the concentration of inducible protein 10 (IP-10) present in a test sample with the resulting percentage of active reaction vessels. The plot indicates that the assay was conducted under conditions that permit binary readout detection.

FIG. 10 depicts a plot of the concentration of IP-10 present in a sample with the resulting percentage of active reaction vessels. The linear relationship between the percentage of active reaction vessels and the concentration of target in the plot shown in FIG. 10 suggesting that a binary readout detection method can be used for the detection of non-enzyme protein targets using a sandwich detection approach.

BIBLIOGRAPHY

Each of the following references is incorporated by reference in their entirety, for all purposes.

Sano, T.; Smith, C. L.; Cantor, C. R. *Science* 1992, 258, 120-122.

Nam, J. M.; Thaxton, C. S.; Mirkin, C. A. *Science* 2003, 301, 1884-1886.

Niemeyer, C. M.; Adler, M.; Pignataro, B.; Lenhert, S.; Gao, S.; Chi, L. F.; Fuchs, H.; Blohm, D. *Nucleic Acids Research* 1999, 27, 4553-4561.

Zhou, H.; Fisher, R. J.; Papas, T. S. *Nucleic Acids Research* 1993, 21, 6038-6039.

Niemeyer, C. M.; Adler, M.; Wacker, R. *Trends in Biotechnology* 2005, 23, 208-216.

Whitesides, G. M. *Nature Biotechnology* 2003, 21, 1161-1165.

Rondelez, Y.; Tresset, G.; Tabata, K. V.; Arata, H.; Fujita, H.; Takeuchi, S.; Noji, H. *Nature Biotechnology* 2005, 23, 361-365.

Nakano, M.; Komatsu, J.; Matsuura, S.; Takashima, K.; Katsura, S.; Mizuno, A. *Journal of Biotechnology* 2003, 102, 117-124.

Nagai, H.; Murakami, Y.; Yokoyama, K.; Tamiya, E. *Biosensors and Bioelectronics* 2001, 16, 1015-1019.

Lipman, A. E.; Shuler, B.; Bakajin, O.; Eaton, W. A. *Science* 2003, 301, 1233-1235.

Chiu, D. T.; Wilson, C. F.; Ryttsen, F.; Stromberg, A.; Farre, C.; Karlsson, A.; Nordholm, S.; Gaggar, A.; Modi, B. P.; Moscho, A.; Garza-Lopez, R. A.; Orwar, O.; Zare, R. N. *Science* 1999, 283, 1892-1895.

Rissin, D. M.; Walt, D. R. *Journal of the American Chemical Society* 2007, 128(19) 6286-6287.

Pantano, P.; Walt, D. R. *Chemistry of Materials* 1996, 8, 2832-2835.

Monk, D. J.; Ueberfeld, J.; Walt, D. R. *Journal of Materials Chemistry* 2005, 15, 4361-4366.

Song, L. N.; Ahn, S.; Walt, D. R. *Emerging Infectious Diseases* 2005, 11, 1629-1632.

Lee, J. Y.; Li, H. W.; Yeung, E. S. *Journal of Chromatography A* 2004, 1053, 173-179.

Xue, Q. F.; Yeung, E. S. *Nature* 1995, 373, 681-683.

Foquet, M.; Korlach, J.; Zipfel, W. R.; Webb, W. W.; Craighead, H. G. *Analytical Chemistry* 2004, 76, 1618-1626.

Gratzl, M.; Lu, H.; Matsimoto, T.; Yi, C.; Bright, G. R. *Analytical Chemistry* 1999, 71, 2751-2756.

Stamou, D.; Duschl, C.; Delamarche, E.; Vogel, H. *Angewandte Chemie-International Edition* 2003, 42, 5580-5583.

Gosalia, D. N.; Diamond, S. L. *Proceedings of the National Academy of Sciences USA* 2003, 100, 8721-8726.

Lu, H. P.; Xun, L. Y.; Xie, X. S. *Science* 1998, 282, 1877-1882.

Taylor, J. R. *An Introduction to Error Analysis*; Second Addition ed.; University Science Books: Sausalito, C A, 1997.

Wheeler, A. R.; Throndset, W. R.; Whelan, R. J.; Leach, A. M.; Zare, R. N.; Liao, Y. H.; Farrell, K.; Manger, I. D.; Daridon, A. *Analytical Chemistry* 2003, 75, 3581-3586.

The invention claimed is:

1. A method of determining the concentration of an analyte in a fluid sample to be tested, the method comprising the steps of:
   (a) partitioning at least a portion of the analyte molecules in the fluid sample across a plurality of reaction vessels so that more than 20% but less than 95% of the reaction vessels contain at least one molecule, wherein the analyte is attached to a nanoparticle or microparticle by a capture component;
   (b) determining the presence or absence of the analyte in each reaction vessel to identify the number of reaction vessels that contain analyte and/or to identify the number of reaction vessels that contain no analyte; and
   (c) determining the concentration of the analyte in the fluid sample by a Gaussian distribution analysis of the number of reaction vessels that contain the analyte.

2. The method of claim 1, wherein, in step (a), more than 20% but less than 60% of the reaction vessels contain at least one molecule.

3. The method of claim 1, wherein, in step (a), more than 60% but less than 95% of the reaction vessels contain at least one molecule.

4. The method of claim 1, wherein, in step (a), the sample to be tested is partitioned into at least 1,000 reaction vessels.

5. The method of claim 1, wherein, in step (a), the sample to be tested is partitioned into from 10,000 to 200,000 reaction vessels.

6. The method of claim 5, wherein the sample to be tested is partitioned into from 50,000 to 100,000 reaction vessels.

7. The method of claim 1, wherein the analyte is a biomolecule.

8. The method of claim 7, wherein the biomolecule is selected from the group consisting of a protein, a nucleic acid, a lipid, and a carbohydrate.

9. The method of claim 1, wherein the reaction vessels have a volume of from 10 attoliters to 50 picoliters.

10. The method of claim 1, wherein at least a portion of the reaction vessel is defined by a distal end of an optical fiber.

* * * * *

UNITED STATES PATENT AND TRADEMARK OFFICE
CERTIFICATE OF CORRECTION

PATENT NO.         : 9,809,838 B2
APPLICATION NO.    : 15/290939
DATED              : November 7, 2017
INVENTOR(S)        : David R. Walt et al.

Page 1 of 1

It is certified that error appears in the above-identified patent and that said Letters Patent is hereby corrected as shown below:

In the Specification

At Column 1, Line 18, the words "Contract No. N00014-01-1" should read --Contract No. N00014-01-1-0659--

Signed and Sealed this
Second Day of July, 2019

Andrei Iancu
*Director of the United States Patent and Trademark Office*